United States Patent [19]

Schenk et al.

[11] Patent Number: 5,397,334
[45] Date of Patent: Mar. 14, 1995

[54] DISTAL MOVEMENT LIMITING ASSEMBLY FOR FINGER STICK DEVICE

[75] Inventors: Robert W. Schenk, Ballwin; Alan B. Ranford, St. Louis; Shawn C. Ray, St. Charles, all of Mo.

[73] Assignee: Sherwood Medical Company, St. Louis, Mo.

[21] Appl. No.: 180,169

[22] Filed: Jan. 11, 1994

[51] Int. Cl.⁶ .......................................... A61B 17/34
[52] U.S. Cl. .................................................. 606/182
[58] Field of Search ................ 128/760, 770; 606/181, 606/182; 604/192, 194, 198

[56] References Cited

U.S. PATENT DOCUMENTS

| | | | |
|---|---|---|---|
| 3,358,689 | 12/1967 | Higgins | 128/329 |
| 4,673,399 | 6/1987 | Pruett | 604/272 |
| 4,840,185 | 6/1989 | Hernandez | 128/763 |
| 4,889,117 | 12/1989 | Stevens | 606/181 |
| 4,994,068 | 2/1991 | Hufnagle | 606/181 |
| 5,169,391 | 12/1992 | Vogel | 604/177 |
| 5,196,025 | 3/1993 | Ranallette et al. | 606/182 |
| 5,217,480 | 6/1993 | Haber et al. | 606/182 |

*Primary Examiner*—Max Hindenburg
*Attorney, Agent, or Firm*—Montgomery W. Smith; Curtis D. Kinghorn; David A. Warmbold

[57] ABSTRACT

An assembly for preventing movement of a sharp lancet tip out of a lancet device of the type having a linearly movable and retractable lancet tip is disclosed. The lancet device has a patient contacting or distal end and an opposed proximal end. The lancet device has a lancet that is substantially encased in an elongated molded plastic lancet body. The lancet has a sharp tip that extends beyond the end of the lancet and is enclosed in a removable cap. The distal end of the lancet has a pair of retainer arms that extend away from the lancet body on opposite sides of the lancet body parallel to the axis of the lancet body. The distal end of the retainer arms extend slightly beyond the distal end of the lancet body and are curved toward the axis of the lancet body to contact the outer surface of the cap. Each retainer arm has a stop, located near the distal end of the retainer arms. The distal end of the lancet body fits in a chamber in the lancet device. The chamber has a pair of retainer arm supports located along opposite sides of the inner surfaces of the chamber. These retainer arm supports jut away from the inner surfaces at an obtuse angle. The retainer arm supports abut the corresponding stops along the distal surface of the stops.

12 Claims, 22 Drawing Sheets

DISTAL MOVEMENT LIMITING ASSEMBLY FOR FINGER STICK DEVICE

BACKGROUND OF THE INVENTION

1. Field of the Invention

The invention relates to an assembly for selectively preventing the linear motion of a lancet in a device for producing a drop of blood for blood sampling.

2. Description of Related Art

Lancets are used to pierce the skin of a patient, usually through the finger. Blood then flows through the incision where it is collected for testing in a blood collection tube such as a capillary tube or pipette.

Historically, early lancets generally had a handle and a sharp lancet tip extending therefrom. However, numerous problems are inherent with such lancets such as controlling the depth and angle of penetration by the lancet tip, controlling the force of the insertion, and the psychological affect to the user of seeing the exposed lancet tip.

One attempt to avoid these and other problems with this early type of lancet was to create lancets having lancet tips that are spring loaded to be injected into and removed from the patient's skin in a linear direction. Typically, these devices hide the lancet tip both before and after the incision is made to prevent its view by the patient, to minimize trauma to the patient and to prevent inadvertent contact with the lancet. Examples of such a lancet injector are disclosed in U.S. Pat. No. 4,580,565 issued on Apr. 8, 1986 and its parent application U.S. Pat. No. 4,503,856, issued on Mar. 12, 1985, both of which are issued to W. D. Cornell and C. Evans and assigned to the assignee of the present invention.

Other examples of lancet devices that move the lancet tip in a linear direction into and out of contact with a patient's tissue are disclosed in U.S. Pat. No. 4,924,879 issued to W. J. O'Brien on May 15, 1990 and U.S. Pat. No. 5,196,025 issued to Ranalletta et al. on Mar. 23, 1993. In the O'Brien device, the lancet tip moves by being acted upon by a connecting rod connected to the outer edge of a rotating wheel. As the wheel rotates, the lancet tip is moved in a reciprocating fashion. The lancet tip is constrained to linear motion by a pair of rollers positioned on either side of the lancet.

In the Ranalletta device, the lancet tip is moved by the straightening of a pair of pivoting arms. The pivoting arms are normally aligned at an angle with respect to each other. As the arms are straightened, the lancet tip is moved. The lancet tip is constrained to linear movement by a guide bore that conformably holds and positions the lancet.

The lancet body is preferably sterilized at the time of manufacture. In many devices a cap surrounds and encases the distal tip of the lancet. The cap prevents inadvertent contact with the distal tip of the lancet and also preserves the sterility of the lancet tip. The cap is placed over and sealed to the lancet body to preserve the sterile condition of the distal tip of the lancet until the cap is removed prior to the use of the device.

The cap is usually simultaneously molded with the lancet body so that a break point connects the cap with the lancet body. The break point is usually a narrowed portion of the material of the cap and the lancet body. The break point breaks when the cap is twisted. The cap is then removed from around the distal tip of the lancet to expose the sharp pointed distal tip of the lancet.

None of the devices having a cap covering the distal tip of the lancet have means to prevent the lancet from moving out of the lancet device until it is desired to use the lancet device.

SUMMARY OF THE INVENTION

An assembly for preventing movement of a sharp lancet tip out of a lancet device of the type having a linearly movable and retractable lancet tip is disclosed. The lancet device has a patient contacting or distal end and an opposed proximal end.

The lancet device has a lancet that is substantially encased in an elongated molded plastic lancet body. The distal end of the lancet has a pair of retainer arms that extend away from the lancet body on opposite sides of the lancet body parallel to the axis of the lancet body. The distal end of the retainer arms extend slightly beyond the distal end of the lancet body and are curved toward the axis of the lancet body to contact the outer surface of the cap. Each retainer arm has a stop that extends from each of the retainer arms away from the axis of the lancet body. The stops are located near the distal end of the retainer arms.

The distal end of the lancet body fits in a chamber that has a width sufficiently large to allow the retainer arms and stops to fit within the chamber. The chamber has a pair of retainer arm supports located along the inner surfaces of the chamber on opposite sides of the recesses of the chamber. These retainer arm supports jut away from the inner surfaces at an obtuse angle as viewed by moving distally along the inner surfaces. The retainer arm supports abut the corresponding stops along the distal surface of the stops.

With the cap in place around the distal tip of the lancet, any force applied to the lancet body by the lancet device to move the lancet body distally causes the stops to contact the retainer arm supports. However, because the retainer arm supports are angled, as the stops are pressured to move distally, contact between the stops and the retainer arm supports deflects the stops toward the axis of the lancet body. But, the distal ends of the retainer arms contact the outer surface of the cap so that the stops cannot move clear of contact with the retainer arm supports. As a result, the contact between the stops and the retainer arm supports prevents the retainer arms, and consequently the lancet body, from moving distally.

After the cap is removed so that the lancet device may be used to produce a drop of blood from a patient, the device puts pressure on the lancet body to move it distally. Distal pressure on the lancet body is transferred to the retainer arms and to the stops.

As the stops are pressured to move distally, contact between the retainer arm supports and the stops again causes the stops to deflect toward the axis of the lancet body. Now, however, the distal ends of the retainer arms do not contact the outer surface of the cap, but instead may move toward the axis of the lancet body. As the distal end of the retainer arms moves toward the axis of the lancet body, the stops move clear of the retainer arm supports. As a result, the retainer arms, and consequently the lancet body, may move distally so that the distal tip of the lancet may move beyond the distal end of the device.

It is therefore an object of the invention to provide an assembly for a device for producing a drop of blood by moving a lancet tip linearly into and out of contact with a patient that prevents undesired or untimely movement of the lancet tip.

It is another object of the invention to provide an assembly for a device for producing a drop of blood by moving a lancet tip linearly into and out of contact with a patient that prevents injury to the user or others before the device is in operation to produce the drop of blood.

It is another object of the invention to provide an assembly for a device for producing a drop of blood by moving a lancet tip linearly into and out of contact with a patient that preserves the sterility of the device until it is desired to produce a drop of blood from a patient.

It is another object of the invention to provide an assembly for a device for producing a drop of blood by moving a lancet tip linearly into and out of contact with a patient that is simple to use and inexpensive to manufacture.

DETAILED DESCRIPTION OF THE INVENTION

The invention is intended to be used with any lancet type device that moves a lancet tip in a linear direction into and out of contact with a patient's tissue. As explained above. The preferred embodiment of the lancet type device is disclosed in detail hereafter. Other examples of such devices are disclosed in U.S. Pat. Nos. 4,503,856 and 4,580,565 issued on Mar. 12, 1985 and Apr. 8, 1986, respectively, to W. D. Cornell and C. Evans, U.S. Pat. No. 4,503,856, issued to W. D. Cornell and C. Evans on Mar. 12, 1985, U.S. Pat. No. 4,924,879 issued to W. J. O'Brien on May 15, 1990 and U.S. Pat. No. 5,196,025 issued to Ranalletta et al. on Mar. 23, 1993. These patents are incorporated herein by reference as teaching alternate methods of providing linear motion to a lancet tip.

Figure 1:
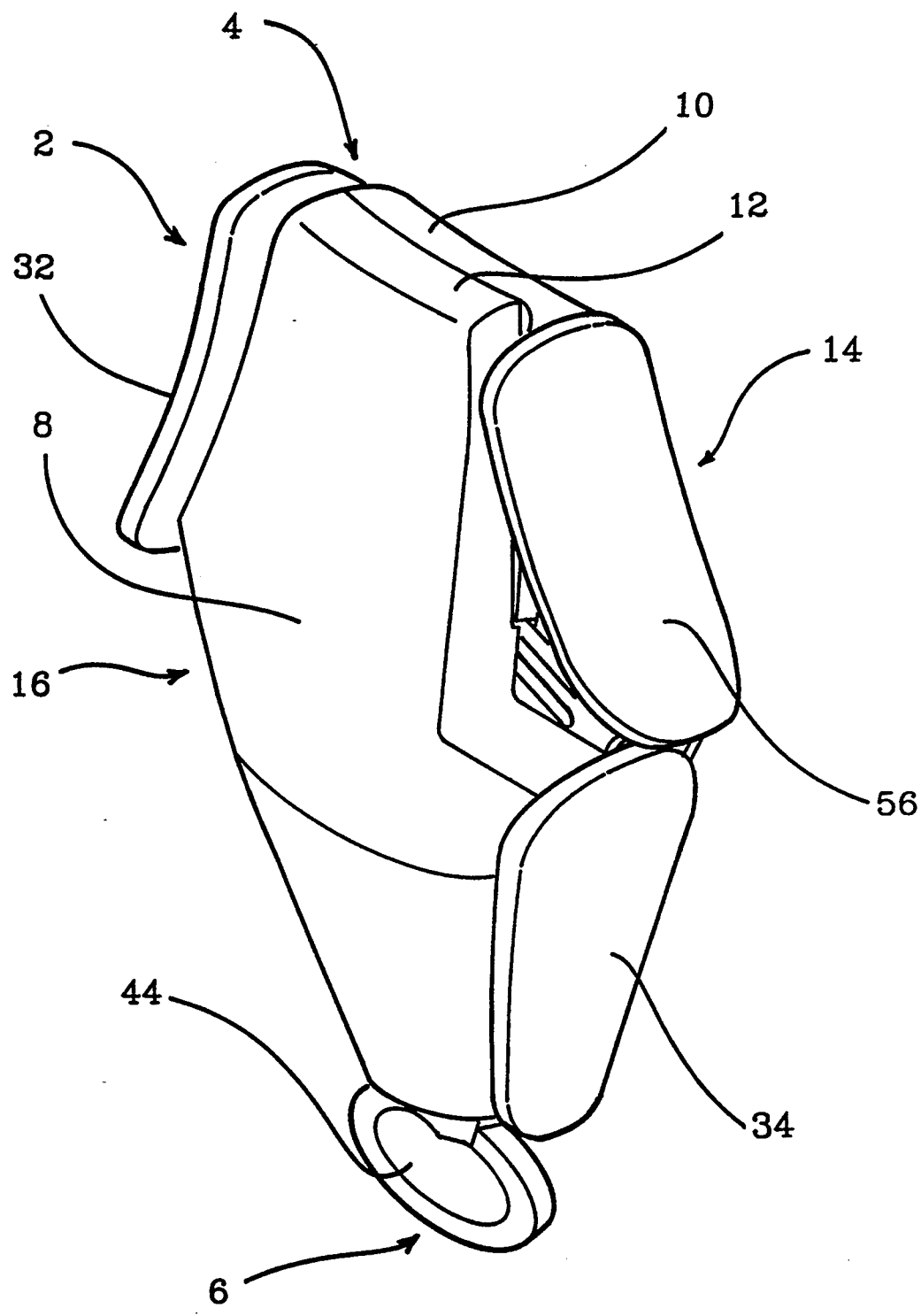
FIG. 1 is a perspective view of the fully assembled embodiment of the lancet device in the "ready to use" position.

A preferred embodiment of a device that moves a lancet tip in a linear direction into and out of contact with a patient's tissue is disclosed hereafter to illustrate the invention. FIG. 1 is a perspective view of this preferred embodiment of a lancet device, generally labeled 2. FIG. 1 shows the exemplary device in an assembled configuration.

The device 2 disclosed herein is disclosed to illustrate the workings of the invention. However, it is to be clearly understood that the invention is not limited in use to the device 2 shown but may be used on any lancet device that moves a lancet tip in a linear direction.

Device 2 has a proximal end 4 and a patient contacting distal end 6. Distal refers to the direction generally away from the user of the device and toward the patient. Throughout this description, reference to the proximal and the distal ends of the elements refers to the ends of the elements closest to the proximal and distal ends 4, 6 of the device 2, respectively.

Further, throughout this description, similar elements are referred to by similar reference numbers. As a result, the description of an element and its function given in one location of the description applies to the element referred to elsewhere in the description with the same reference number except where minor changes must be made to the element or its function as specifically set out in the description or as will be clear to those skilled in the art.

Figure 2:
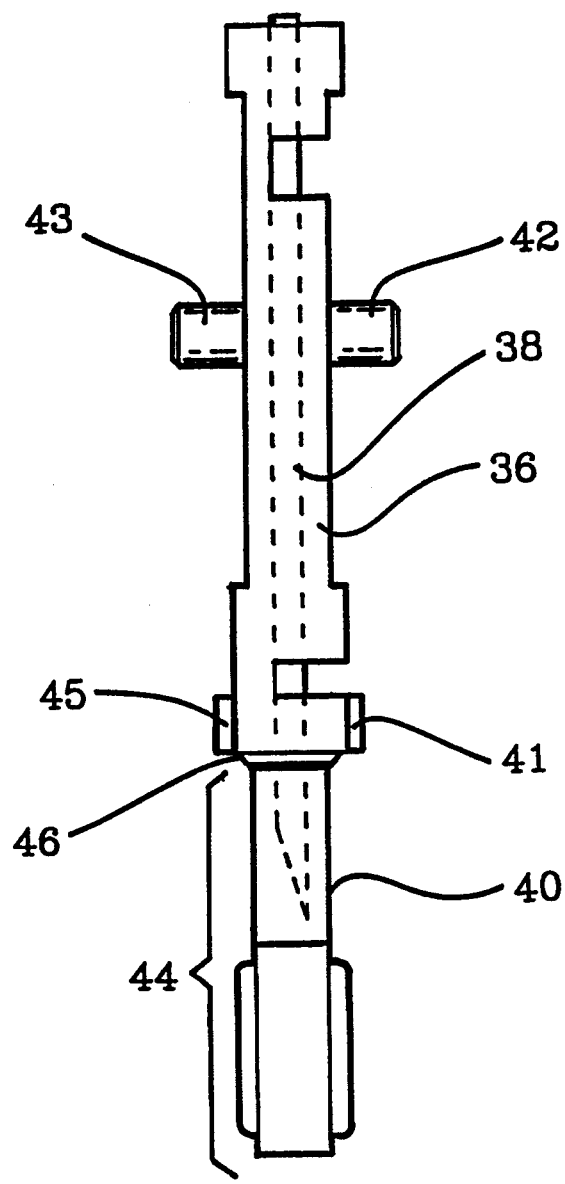
FIG. 2 is a side elevational view of the lancet body and cam follower of the lancet device.

The device 2 includes an elongated cylindrical lancet body 36 (FIG. 2) that substantially encases a lancet 38 (shown substantially in phantom in FIG. 2). Although lancet body 36 is preferably cylindrical, lancet body may also have cross sections other than cylindrical such as square, rectangular and oval, to name but a few.

Lancet 38 is preferably insert molded in lancet body 36 by techniques well understood in the art. Lancet 38 has an distal tip 40 extending distally beyond lancet body 36. The distal tip 40 of lancet 38 is ground to a sharp point so that when the patient's skin is penetrated by the distal tip 40 to produce blood as described hereafter, the distal tip 40 will produce the least trauma to the patient.

Preferably, a pair of recess guide pins 41, 45 extend from lancet body 36 near the distal end of lancet body 36. Recess guide pins 41, 45 are preferably integrally formed with lancet body 36 and protrude from lancet body 36 at approximately a right angle.

A cam follower 42 extends from lancet body 36 about midway long lancet body 36. Cam follower 42 is preferably cylindrical and is integrally formed with lancet body 36. Cam follower 42 protrudes from lancet body 36 at approximately a right angle.

Also preferably, a positioning guide pin 43 extends from lancet body 36 opposite cam follower 42. Positioning guide pin 43 is also preferably cylindrical, integrally formed with lancet body 36 and protrudes from lancet body 36 at approximately a right angle. Cam follower 42 and positioning guide pin 43 have identical diameters and lengths.

Lancet body 36 also includes a cap 44 that surrounds and encases the distal tip 40 of lancet 38. Cap 44 is preferably simultaneously molded with lancet body 36 so that a break point 46 connects cap 44 with lancet body 36. Break point 46 is preferably a narrowed portion of the material of cap 44 and lancet body 36 that breaks when cap 44 is twisted. Cap 44 may then be removed from around the distal tip 40 of lancet 38 to expose the sharp pointed distal tip 40 of lancet 38. Lancet body 36 is preferably sterilized at the time of manufacture so that cap 44 preserves the sterile condition of distal tip 40 until cap 44 is removed prior to the use of the device 2.

Figure 3:
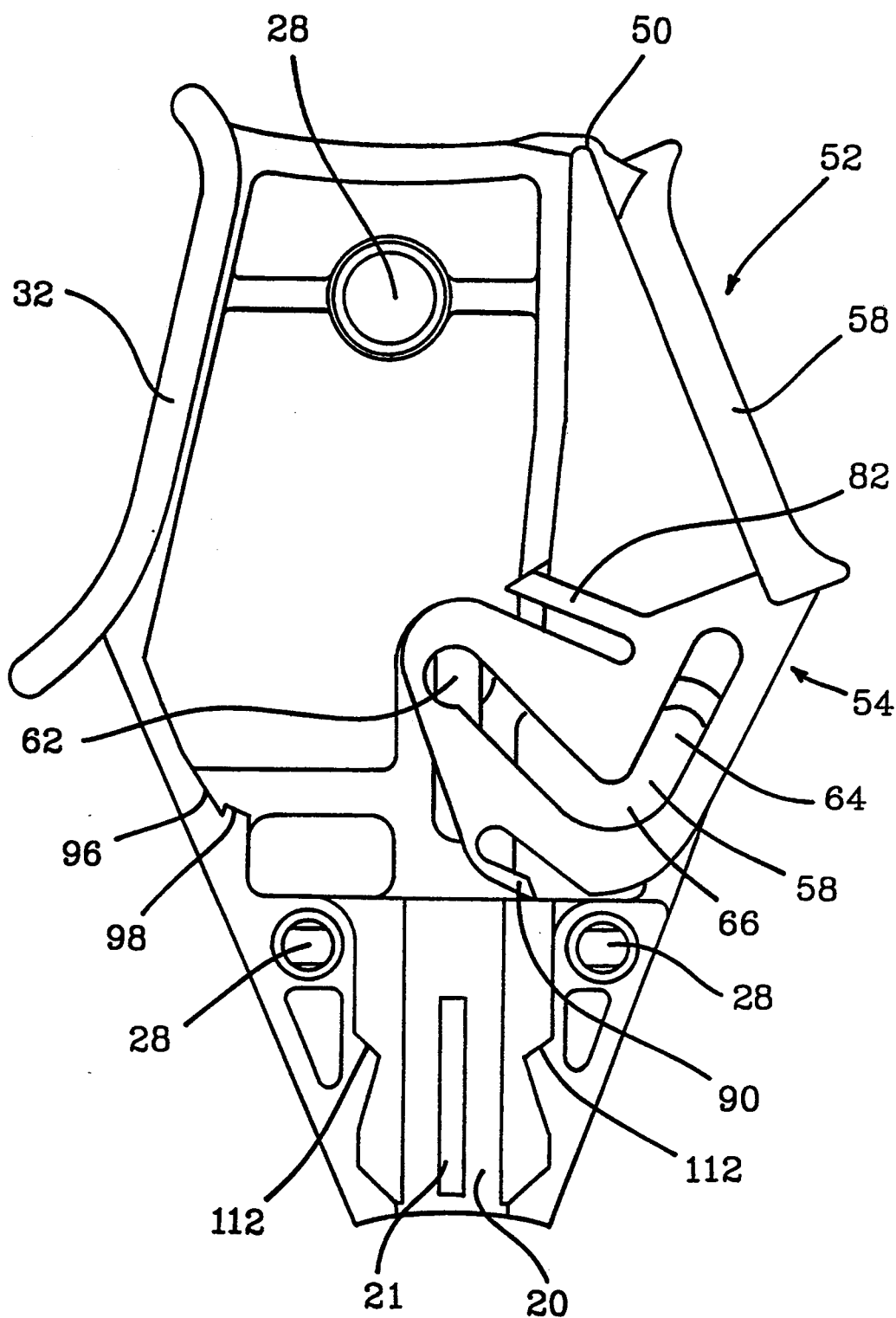
FIG. 3 is a plan view of the lower section with the arm in place to receive the cam follower.
Figure 4:
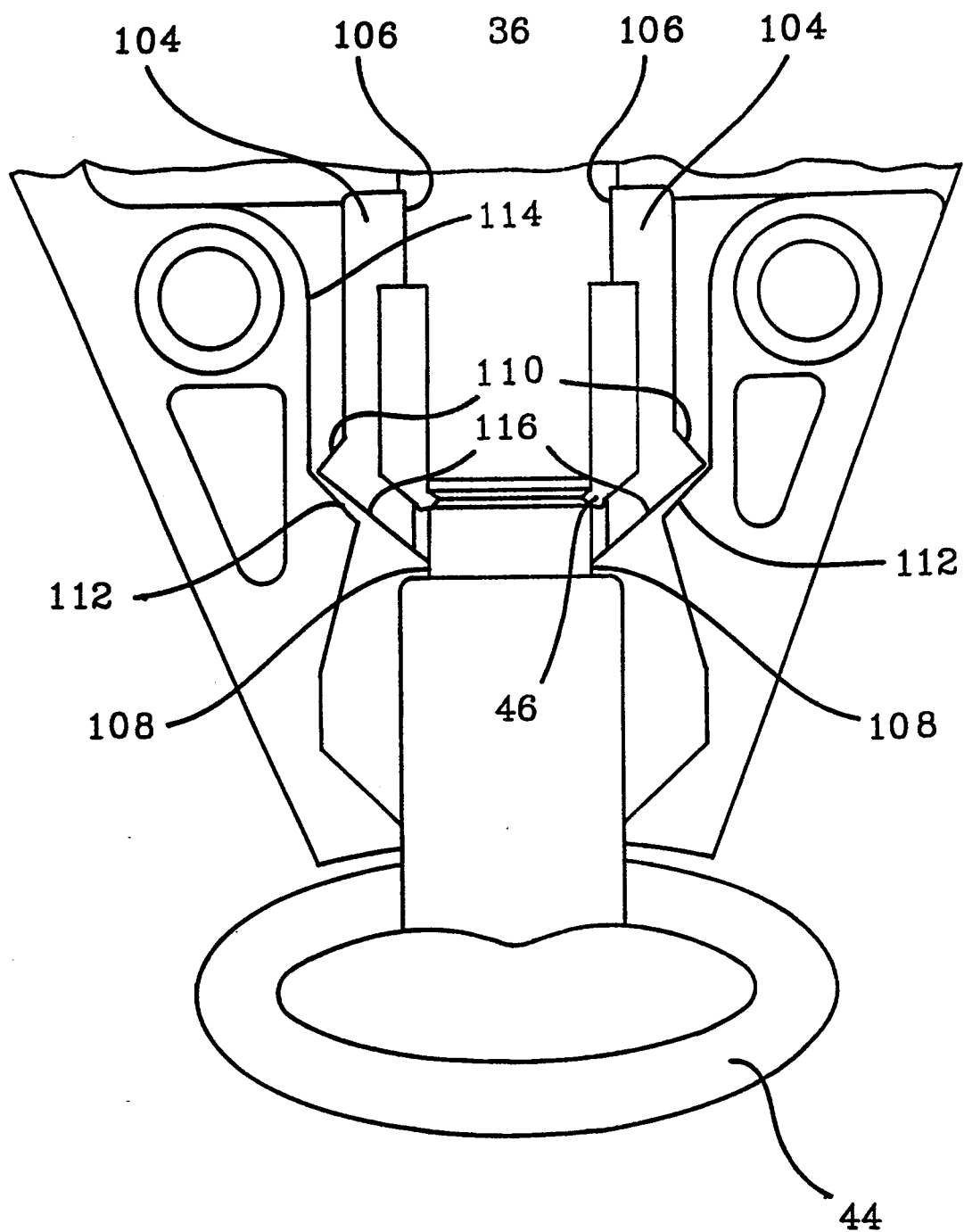
FIG. 4 is an enlarged plan view of the invention of FIG. 3.

In the invention, as shown in FIG. 3 and in detail in FIG. 4, the distal end of the lancet body 36 has a pair of retainer arms 104. Retainer arms 104 extend away from and are offset from the outer surface 106 of lancet body 36 on opposite sides of lancet body 36, substantially parallel to the axis of the lancet body 36. The proximal end of retainer arms 104 connect to lancet body 36 proximal to the distal end of lancet body 36. The distal end of retainer arms 104 extend slightly beyond the distal end of the lancet body 36 and are curved toward the axis of the lancet body 36 to contact the outer surface 108 of cap 44.

A stop 110 extends from each of the retainer arms 104 in a direction radially away from the axis of the lancet body 36.

Figure 5:
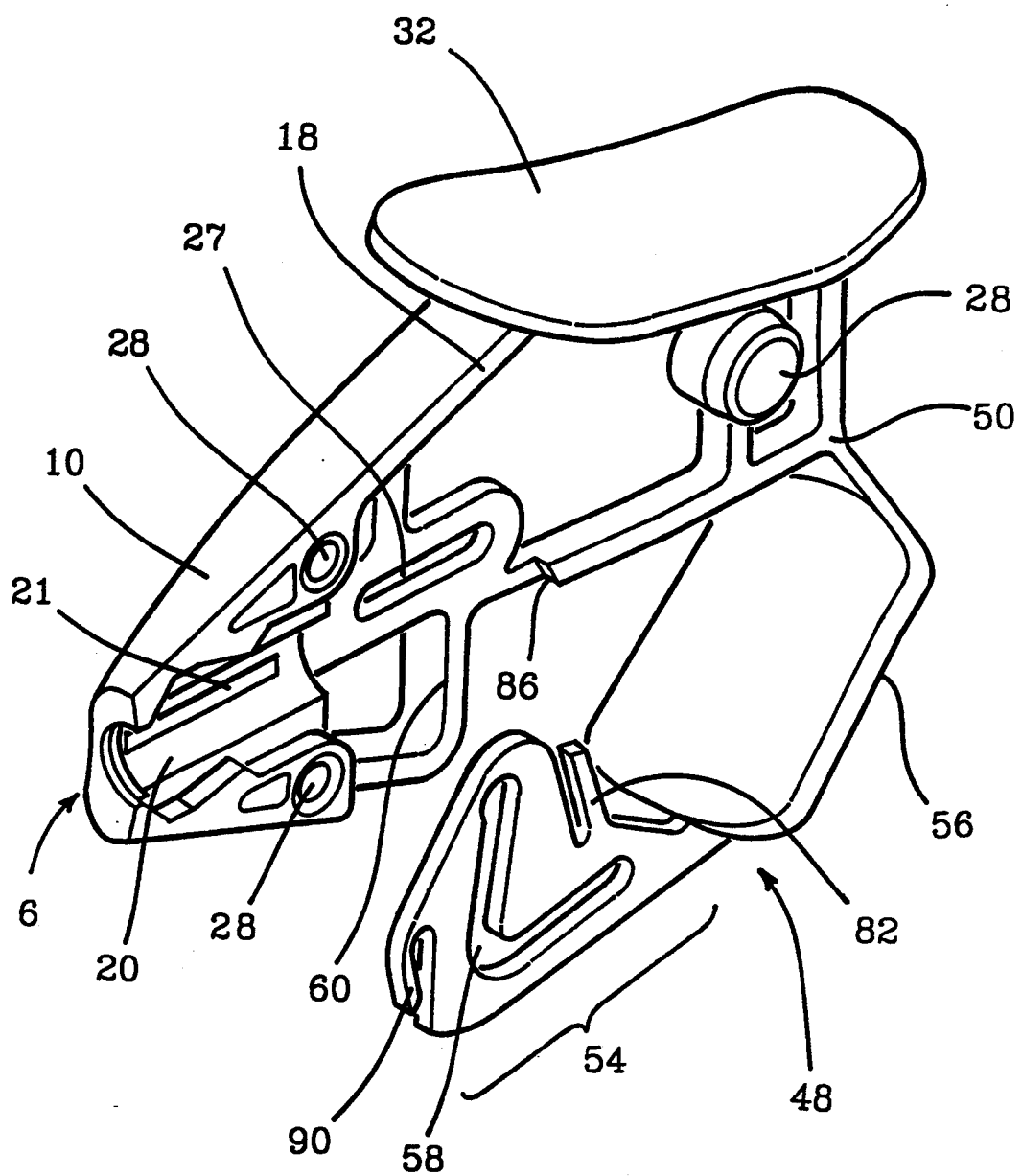
FIG. 5 is a perspective view of the lower section.
Figure 6:
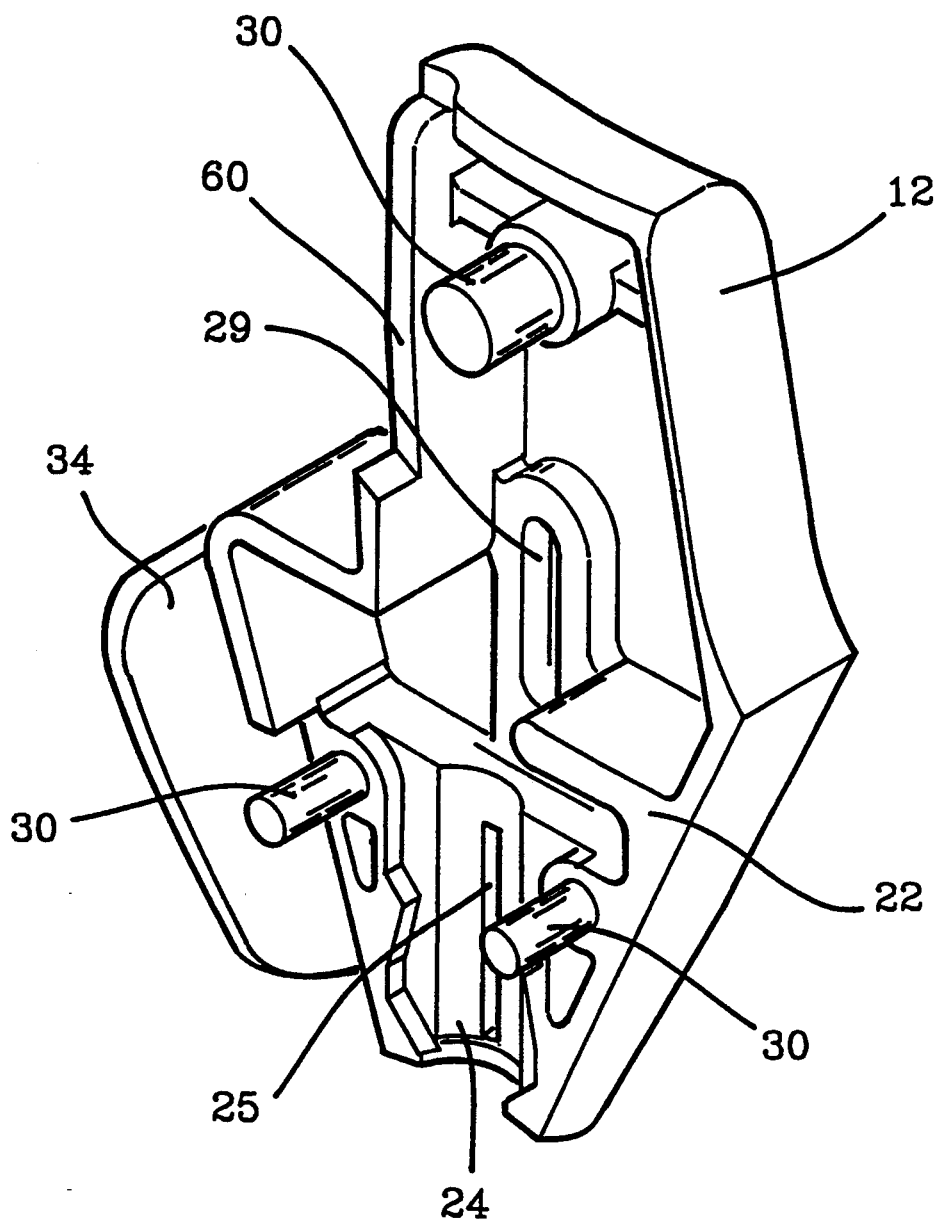
FIG. 6 is a perspective view of the upper section.
Figure 7:
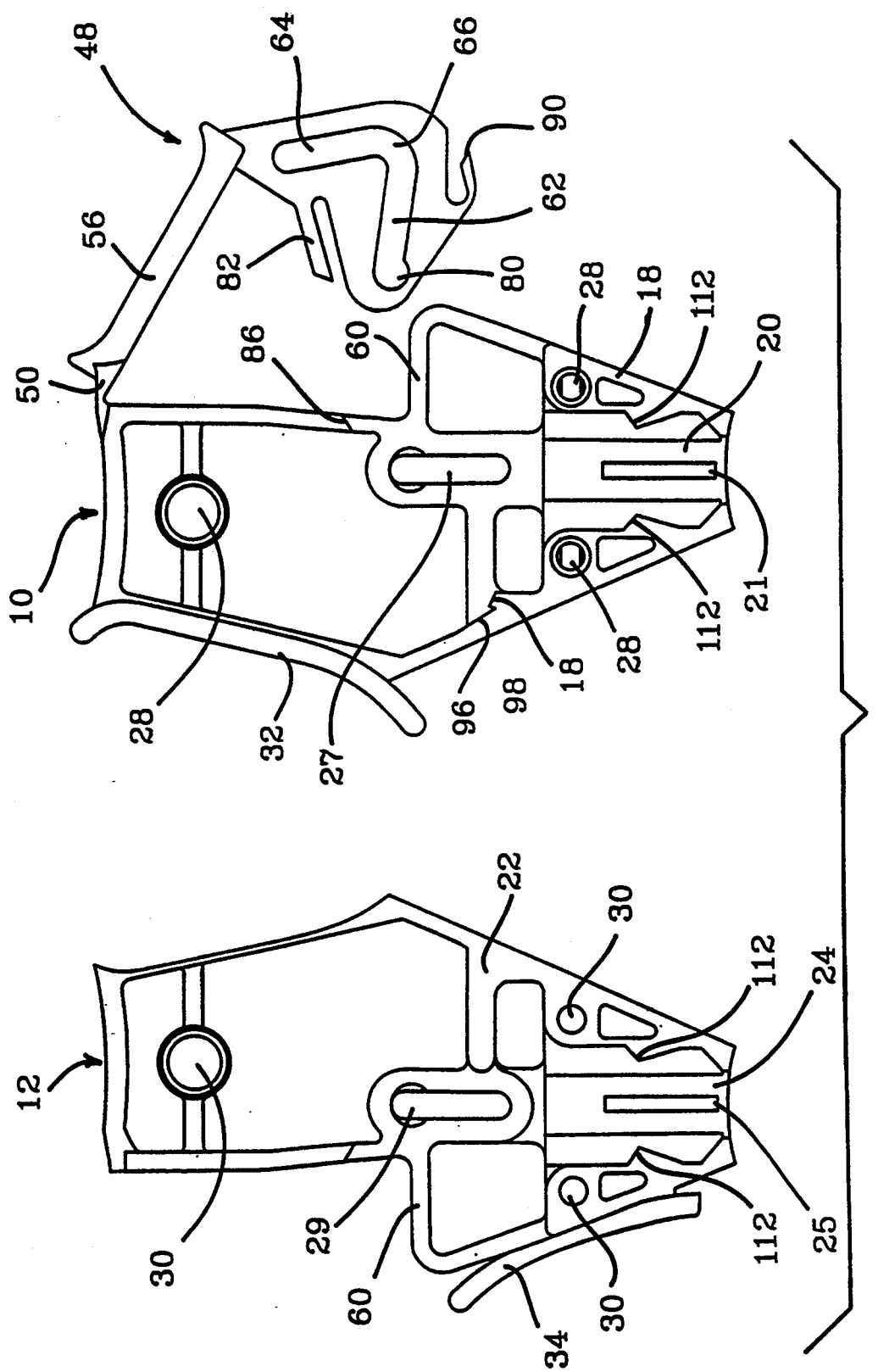
FIG. 7 is a plan view of the case of the lancet device in an open position.

The device 2 includes a case 8 having a lower section 10 and an opposed congruent upper section 12. As seen in FIGS. 5, 6 and 7, lower section 10 and upper section 12 are each substantially concave shaped. As a result, when lower section 10 and upper section 12 are joined together, as will be described hereafter, they form a substantially hollow case 8. As a result, when lower section 10 and upper section 12 are joined together, as will be described hereafter, they form a substantially hollow case 8.

Lower section 10 also has a generally planar outer edge 18 (FIG. 5) that extends around the outer periphery of the lower section 10. A lower section recess 20 is formed in the interior of lower section 10 extending from the distal end 6 proximally. Lower section recess 20 is half cylindrical and open at its distal end 6. The central axis of lower section recess 20 is aligned with the planar outer edge 18 of lower section 10.

As shown in FIG. 6, upper section 12 has a generally planar outer edge 22 that extends around the outer periphery of the upper section 12. Upper section 12 also has an elongated upper section recess 24 that extends from the distal end 6 of upper section 12 toward the proximal end 4 of upper section 12. Upper section recess 24 is also approximately half cylindrical so that the central axis of upper section recess 24 is aligned with the planar outer edge 22 of upper section 12. Upper section recess 24 is also open at its distal end 6.

In the invention, the distal end of both lower and upper section recesses 20, 24 are enlarged just proximal to the distal end of the recess 20, 24 to have a width sufficiently large to allow the retainer arms 104 and stop 110 to fit within and move along recesses 20, 24 as the device 2 moves from the "ready to use" to the "used and locked" position as described hereafter.

Also, a pair of retainer arm supports 112 are located along the outer surfaces 114 of the enlarged recesses 20, 24 on opposite sides of recesses 20, 24. Retainer arm supports 112 jut away from the outer surfaces 114 at an obtuse angle as viewed by moving distally along the outer surfaces 114. When the device 2 is in the "ready to use" position, retainer arm supports 112 abut the corresponding stops 110 along the distal surface 116 of stops 110.

Both lower and upper sections 10, 12 have a hole 23, 23', respectively, extending into their outer surfaces for a purpose that will be described hereafter. Holes 23, 23' are preferably tapered but may also have a "cloverleaf" shape.

Lower and upper section recesses 20, 24 also each have an elongated recess slot 21, 25, respectively, that extends into lower and upper section 10, 12 from the outer edges of lower and upper section recesses 20, 24, respectively. The axes of the recess slots 21, 25 are aligned with the axes of lower and upper section recesses 20, 24, respectively. Recess slots 21, 25 have a width approximately the same as the width of recess guide pins 41, 45, respectively.

Lower and upper section 10, 12 also each have an elongated positioning slot 27, 29 located proximal to lower and upper section recesses 20, 24, respectively. The axis of the positioning slots 27, 29 are aligned with of lower and upper section recesses 20, 24, respectively. Positioning slots 27, 29 have approximately the same width as the diameters of cam follower 42 and positioning guide pin 43.

As described above, cam follower 42 and positioning guide pin 43 have identical diameters and lengths. This allows the lancet body 36 to be oriented in chamber 26 during assembly with cam follower 42 or positioning guide pin 43 interchangeably aligned with positioning slots 27, 29.

Lower section 10 and upper section 12 meet along their outer edges 18, 22 so that a contiguous surface is formed where their respective outer edges 18, 22 meet. When outer edge 22 of upper section 12 is brought into contact with outer edge 18 of lower section 10, a substantially hollow case 8 is formed.

When lower and upper sections 10, 12 meet along their outer edges 18, 22, lower section recess 20 and upper section recess 24 are aligned so that when outer edge 18 contacts outer edge 22, a cylindrical chamber 26 is formed in case 8 that is open at the distal end 6 of the device 2. In addition, positioning slots 27, 29 are positioned in opposition to each other across the axis of lower and upper section recesses 20, 24.

Lancet body 36 has a diameter approximately the same as the diameter of chamber 26 formed between lower and upper recesses 20, 24. Further, whatever the cross sectional shape of lancet body 36, lower and upper recesses 20, 24 should preferably also have a conforming shape.

In operation, as will be described hereafter, lancet body 36 is placed in chamber 26 where its axis is aligned with the axis of chamber 26. Contact between lancet body 36 and chamber 26 constrains lancet body 36 to linear motion within chamber 26 along the mutual axis of lancet body 36 and chamber 26.

When lancet body 36 is placed in chamber 26 with its axis aligned with the axis of chamber 26, cam follower 42 and positioning guide pin 43 contact and are constrained within positioning slots 27, 29, respectively. Also, recess guide pins 41, 45 contact and are constrained within recess slots 21, 25, respectively.

Contact between cam follower 42 and positioning slot 27, positioning guide pin 43 and positioning slot 29, recess guide pin 41 and recess slot 21, and recess guide pin 45 and recess slot 25, respectively, constrains lancet body 36 to linear motion within chamber 26 along the mutual axis of lancet body 36 and chamber 26. Further, this contact prevents lancet body 36 from rotating around its axis within chamber 26.

It is highly desirably to provide both a cam follower 42 and a positioning guide pin 43, along with their corresponding positioning slots 27, 29 in order to precisely position lancet body 36 in chamber 26 and prevent lancet body 36 from rotating around the axis of lancet body 36. However, positioning slot 27 and positioning guide pin 43 and its corresponding positioning slot 29 are not absolutely required in device 2.

Likewise, it is highly desirably to provide recess guide pins 41, 45 and recess slots 21, 25 along with cam follower 42 and positioning guide pin 43 and their corresponding positioning slots 27, 29 in order to more precisely position lancet body 36 in chamber 26 and prevent lancet body 36 from rotating around the axis of lancet body 36. However, recess guide pins 41, 45 with their corresponding recess slots 21, 25, with or without positioning slot 27 and positioning guide pin 43 and its corresponding positioning slot 29 are not absolutely required to use device 2.

When lower section 10 is aligned with upper section 12 so that their outer edges 18, 22 meet, lower section 10 is locked into contact with upper section 12. Locking is preferably done by providing several lock holes 28 in lower section 10 and corresponding lock tabs 30 that extend away from upper section 12. When upper section 12 is pressed into contact with lower section 10, lock tabs 30 mate with lock holes 28.

Lock tabs 30 may be retained within lock holes 28 preferably either by a frictional fit or by upsetting the ends of the lock tabs 30 after closing by means well known in the art including but not limited to heat staking, ultrasonic welding or adhesives. Although lock holes 28 and lock tabs 30 have been described as being part of lower section 10 and upper section 12, respectively, this configuration may be reversed so that lock holes 28 and lock tabs 30 may be part of upper section 12 and lower section 10, respectively.

In the preferred embodiment, both upper section 12 and lower section 10 have finger pads. Lower section 10 has a finger pad 32 located on the proximal end 4 of its non-arm side 16. Finger pad 32 extends from lower section 10 across upper section 12 when upper and lower sections 10, 12 are joined. As a result, finger pad 32 extends across the entire proximal surface on the non-arm side 16 of device 2.

Upper section 12 also has a finger pad 34 located along its distal outer edge 22 on its arm side 14. Finger pad 34 extends from upper section 12 across lower section 10 when lower and upper sections 10, 12 are joined. As a result, when device 2 is fully assembled, finger pad 34 extends across the entire distal surface of case 8 on the arm side 14 of device 2.

An arm 48 is attached to the proximal end 4 of lower section 10 by a hinge 50. Arm 48 includes a finger pad section 52 and a contiguous cam section 54. Finger pad section 52 includes a finger pad 56 along its outer surface. Finger pad 56 extends from finger pad section 52 across upper section 12 when lower and upper sections 10, 12 are joined. As a result, finger pad 56 extends across the arm side 14 of case 8 to the same extent that finger pad 34 extends across the arm side 14 of case 8.

All finger pads 32, 34 and 56 are preferably substantially planar with curved ends. However, finger pads 32, 34 and 56 may also be slightly curved along their entire lengths to allow the user's thumb or forefinger to be more easily retained thereon. Finger pads 32, 34 and 56 may also have means, such as a rough surface, to produce a high friction outer surface to prevent the user's thumb or forefinger from sliding along finger pads 32, 34 and 56.

Cam section 54 is substantially planar and includes a groove 58 that mates with cam follower 42. Cam section 54 moves across the interior of case 8 by pivoting about hinge 50.

Groove 58 preferably has two legs 62, 64 meeting at a common point 66 so that groove 58 is substantially "V" shaped. Groove 58 has a width approximately the same as the diameter of cam 42. Groove 58 is oriented so that the common point 66 is distal to the legs 62, 64. The details of the shape of groove 58 will be given in detail below.

Figure 11:
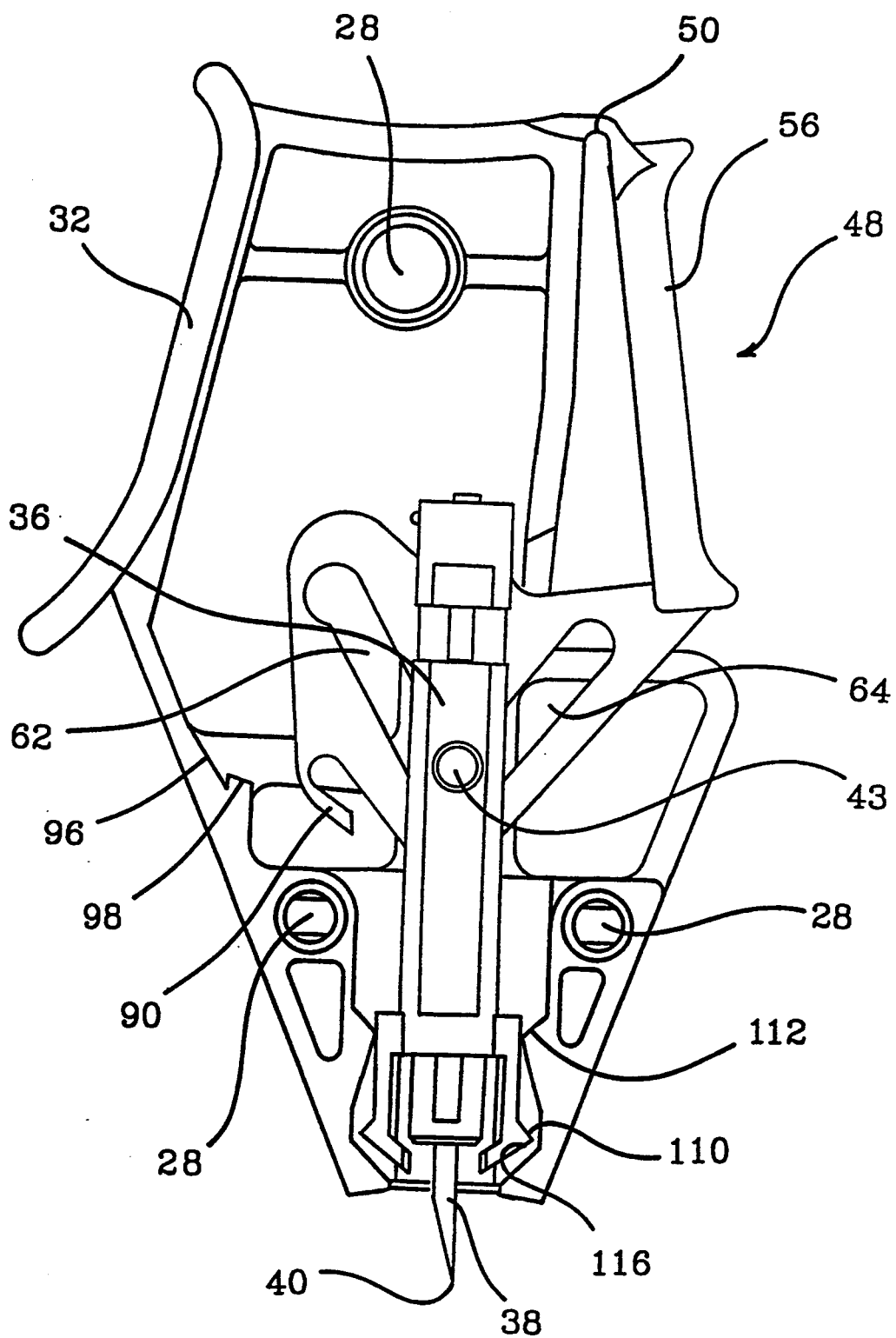
FIG. 11 is a plan view of the case of FIG. 10 with the lancet body in position in the case, the cam follower engaging the groove and the arm in the "lancet most distal" position.
Figure 12:
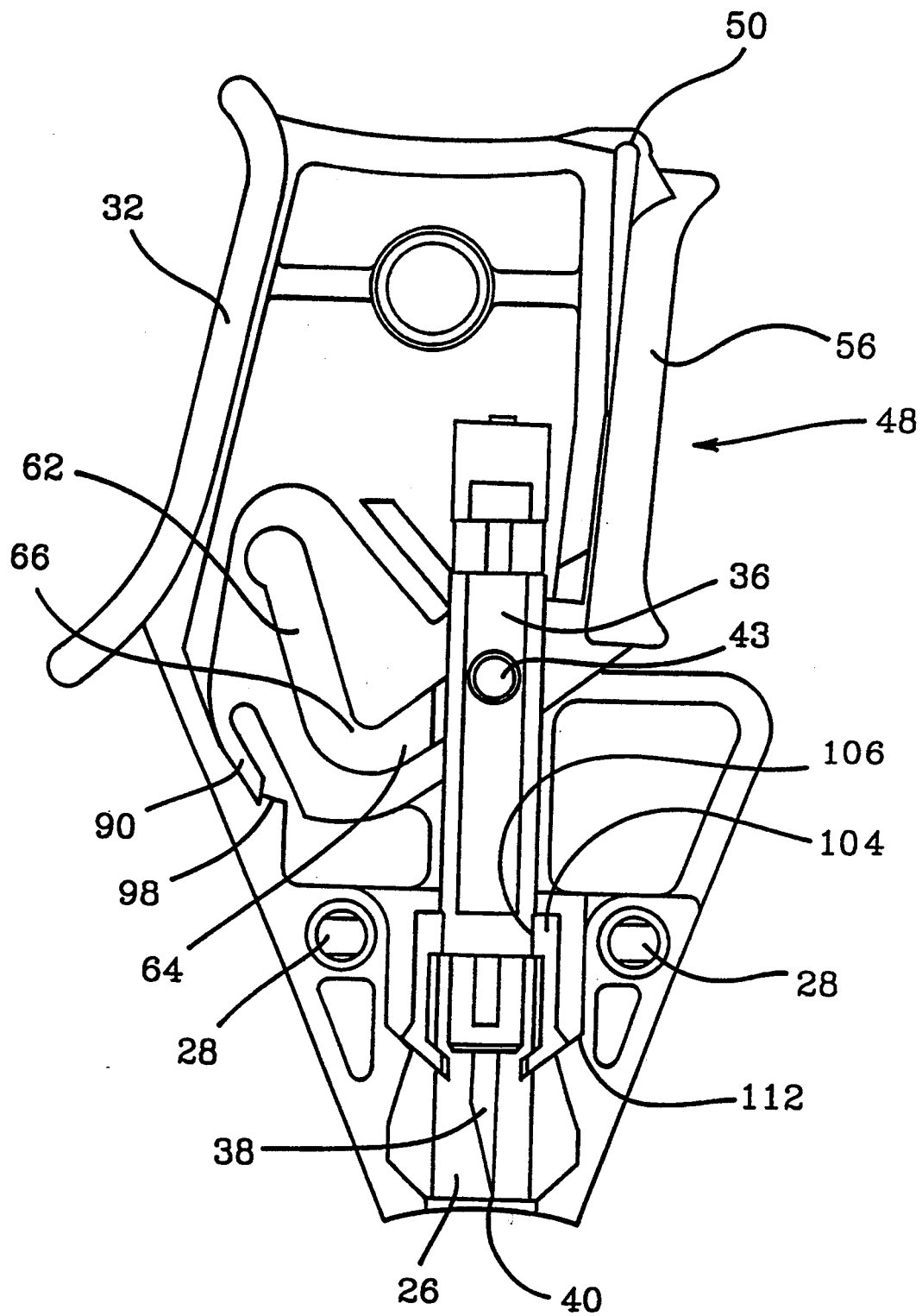
FIG. 12 is a plan view of the case of FIG. 10 with the lancet body in position in the case, the cam follower engaging the groove and the arm in the "used and locked" position.

Hinge 50 is preferably integrally made with case 8 by molding the entire case 8 and arm 48 at the same time by techniques such as injection molding or similar techniques well known in the art. Arm 48 moves from a "ready to use" position (FIG. 10) to a "lancet most distal" position (FIG. 11) to a "used and locked" position (FIG. 12). Contact between cam follower 42 and groove 58, as will be described hereafter, moves lancet body 36, and consequently the distal tip 40 of lancet 38, from a most proximal position to a most distal position and back to a most proximal position corresponding to the "ready to use", "lancet most distal" and "used and locked" positions, respectively.

In operation of the invention with the cap 44 in place around the distal tip 40 of lancet 38, the force applied to the lancet body 36 to move it distally by contact between cam follower 42 and groove 58 causes stops 110 to initially move distally toward the retainer arm supports 112. However, retainer arm supports 112 are angled relative to stops 110. Therefore, as stops 110 move distally, contact with the angled retainer arm supports 112 deflects stops 110 off of retainer arm supports 112 toward the axis of the lancet body 36.

The deflection of stops 110 toward the axis of lancet body 36 tends to move the entire distal end of retainer arm 104 toward the axis of lancet body 36. However, because the distal ends of the retainer arms 104 are already in contact with the outer surface 108 of cap 44, stops 110 are prevented from being further deflected toward the axis of lancet body 36.

The net result of this is that stops 110 cannot move clear of contact with retainer arm supports 112. Consequently, in the "ready to use" position with cap 44 in place around the distal tip 40 of lancet 38, the contact between the stops 110 and the retainer arm supports 112 prevents the retainer arms 104, and consequently the lancet body 36, from moving distally.

After the cap 44 is removed, as described above, so that the device 2 may be used to produce a drop of blood from a patient, pressure is put on the device 2 to move the lancet body 36 distally by squeezing finger pads 32, 34 and 56 together. Distal pressure on the lancet body 36 is transferred to the retainer arms 104 and to the stops 110.

Figure 13:
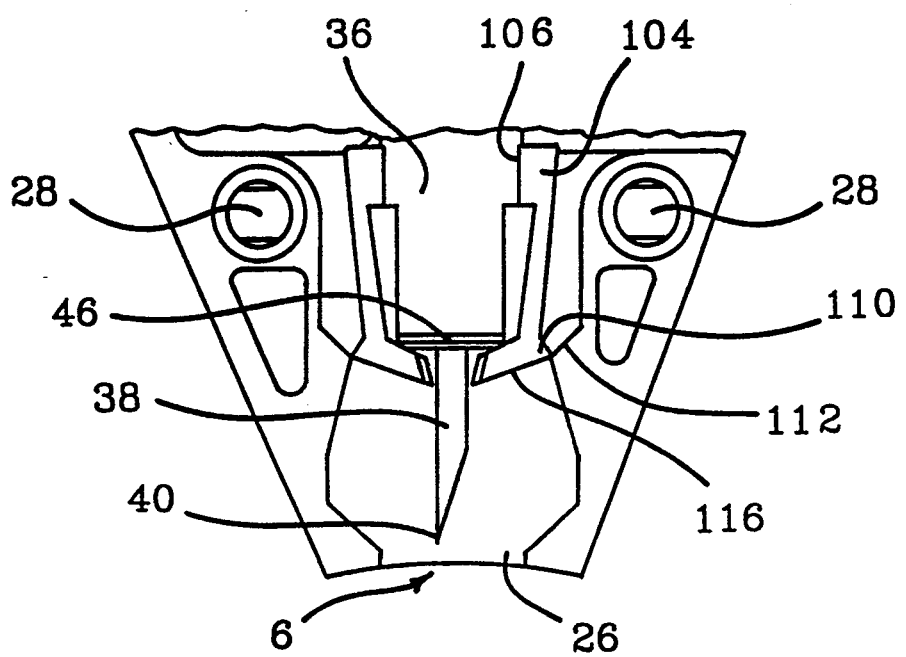
FIG. 13 is a plan view of the invention shown in FIG. 3 with the cap removed and the retainer arms moving past the retainer arm supports.

As stop 110 are pressured to move distally, contact between the retainer arm supports 112 and stops 110 again causes stops 110 to move toward the axis of the lancet body 36. Instead, the distal ends of retainer arms 104 may move toward the axis of the lancet body 36. As the distal end of the retainer arms 104 moves toward the axis of the lancet body 36, stops 110 move clear of the retainer arm supports 112 (FIG. 13). As a result, retainer arms 104, and consequently lancet body 36, may move distally so that the distal tip 40 may move beyond the distal end of the case 8.

The size of the stops 110 and the retainer arm supports 112 are both such that with the cap 44 removed, stops 110 clear the retainer arm supports 112 before the distal end of the retainer arms 104 contacts the distal end 40 of the lancet 38. The size of the stops 110 and the retainer arm supports 112 are both such that with the cap 44 removed, stops 110 clear the retainer arm supports 112 before the distal end of the retainer arms 104 contacts the distal end 40 of the lancet 38

Figure 14:
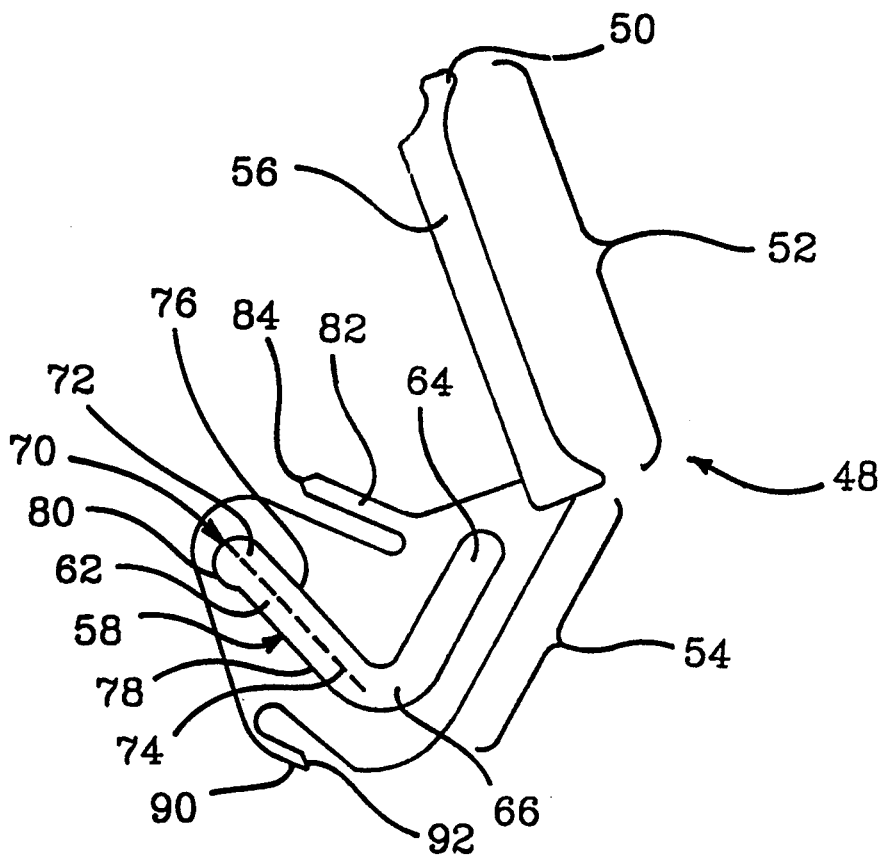
FIG. 14 is a plan view of the arm and groove of the preferred embodiment of the lancet device.
Figure 15:
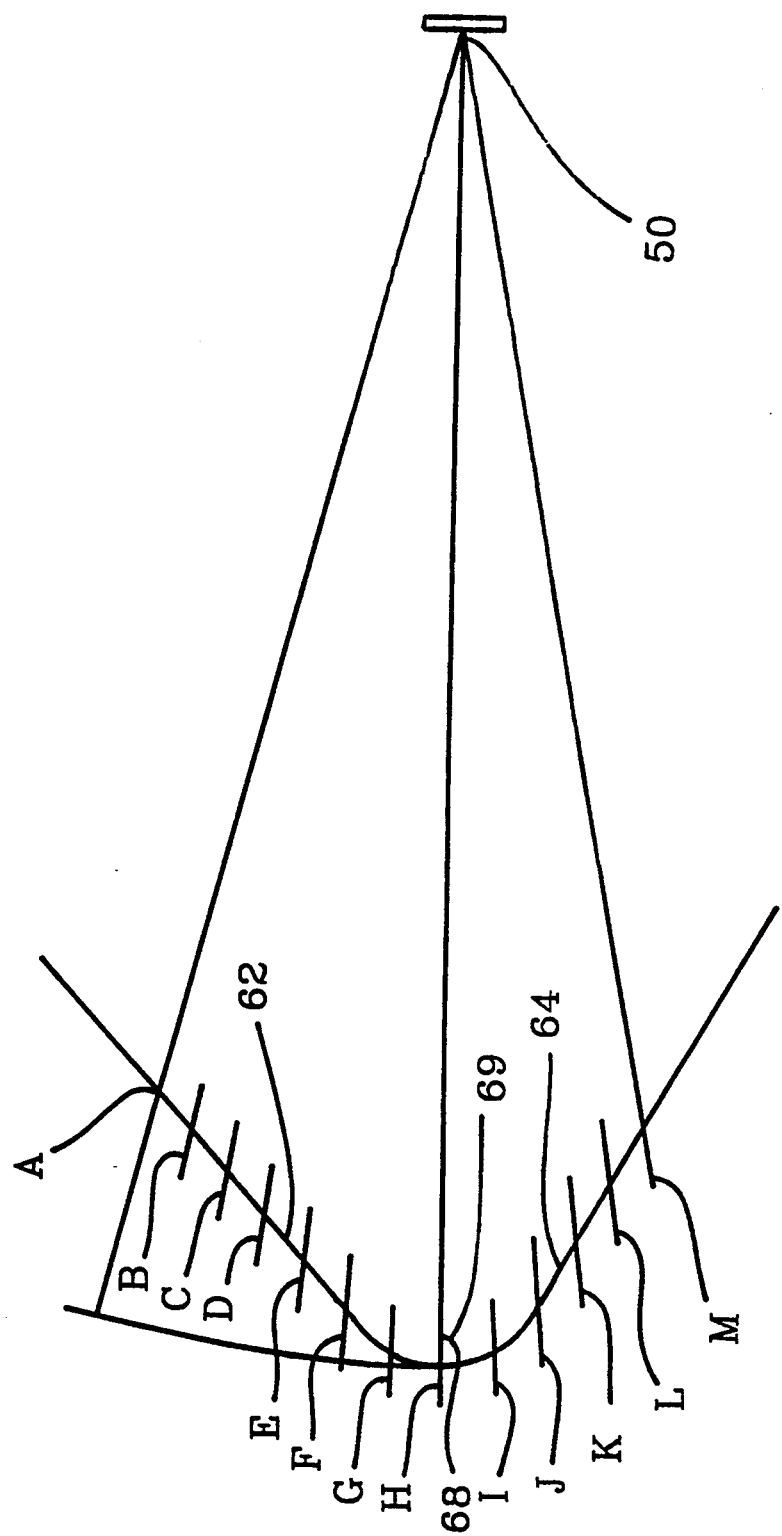
FIG. 15 is a schematic view of the cam follower section and groove of the preferred embodiment of the lancet device.

As stated above, groove 58 includes two legs 62, 64 that meet at a common point 66. In the preferred embodiment, legs 62, 64 are straight. The details of the preferred shape of the groove 58 are shown in FIGS. 14 and 15. The preferred shape was determined with consideration of the following principles and requirements.

It has been found that the preferred amount of rotation of arm 48 around hinge 50 from the "ready to use" to the "already used" positions is about 24°. This allows the user to comfortably handle and use the device 2 as will be described hereafter. Consequently, the shape of groove 58 and its resulting contact with cam 42, as will be described in detail hereafter, must correspond to movement of arm 48 throughout the 24° range.

Further, during movement of arm 48 throughout the 24° range, the distal tip 40 of lancet 38 must move from a most proximal position to a most distal position and back to a most proximal position. The transition from distal movement to proximal movement should be smooth.

Finally, as the distal tip 40 of lancet 38 moves distally, as will be described hereafter, the distal tip 40 will contact and enter the patient's skin. This contact will cause some resistance to further distal movement of the distal tip 40 of lancet 38. After the distal tip 40 has moved to its most distal position in the patient's tissue, the distal tip 40 will be moved proximally.

Movement of the distal tip 40 in the proximal direction will be relatively frictionless because the distal tip 40 will be moving out of the puncture already formed by the distal tip 40 as the distal tip 40 moved distally through the patient's tissue. As a result, a greater mechanical advantage is needed to move the distal tip 40 into contact with the patient's tissue than is required to move the distal tip 40 proximally out of contact with the patient's tissue.

With these principles and requirements in mind and referring to FIG. 15, the 24 degrees of rotation of arm 48 around hinge 50 are shown as radials A–M radiating from hinge 50 in 2° increments. Each of the radials intersects groove 58. More specifically, radials A–G intersect the central axis of leg 62 while radials I–M intersect the central axis of leg 64. Radial H intersects the common point 66.

The radial A corresponds to 0° of rotation which is the "ready to use" position. The radial H corresponds to 14° of rotation which is the "lancet most distal" position. The radial M corresponds to 24° of rotation which is the "used and locked" position.

To increase force available to more easily move the distal tip 40 into contact with the patient's tissue, 14° of rotation of arm 48 moves the distal tip 40 distally and 10° of rotation moves the distal tip 40 proximally. As a result, the distal tip 40 is at the "lancet most'distal" position when the arm 48 has rotated 14° and radial H intersects groove 58. This is the "lancet most distal" position.

In the preferred embodiment of device 2, leg 62, from its intersection with radial A to radial G, and leg 64, from its intersection with radial I to radial M are approximately straight. In this embodiment, the angle between the axes of legs 62, 64 is about 68°. However, because of the geometry of arm 48, hinge 50 and groove 58, the angle of the axes of legs 62, 64 with an axis parallel to the axis of motion of lancet 38 will vary as arm 48 is rotated around hinge 50. This then affects the angle that legs 62, 64 contact cam follower 42 which in turn determines the amount of displacement of cam follower 42 along the axis of lancet 38 per amount of rotation of arm 48 around hinge 50.

In particular, leg 62 intersects an axis 63 parallel to the axis of motion of lancet 38 at an angle that varies smoothly from approximately 40° along the A radial to an angle of approximately 32° along the G radial. Likewise, leg 64, from its intersection with radial I to radial M, is approximately straight. Leg 64 also intersects an axis parallel to the axis of motion of lancet 38 at an angle that varies smoothly from approximately 28° along the I radial to an angle of approximately 52° along the M radial.

Near the "lancet most distal" position, which corresponds approximately to the H radial, legs 62, 64 are deflected from their straight configuration to a curved configuration to allow a smooth transition of cam follower 42 from leg 62 to leg 64. In its simplest form, the curve is formed on an arc 68 having a radius 69 centered on radial H where the radius 69 intersects legs 62, 64 near radials G and I, respectively.

In the preferred embodiment, the distance from hinge 50 to the intersection of groove 58 and radial A is about 0.695". In the "ready to use" position, the distance from the intersection of groove 58 and radial A to the axis of lancet body 36 along a perpendicular to the axis of lancet body 36 is about 0.172". Likewise, in the "ready to use" position, the distance from the intersection of groove 58 and radial M to the axis of lancet body 36 along a perpendicular to the axis of lancet body 36 is about 0.125". The distance of travel of cam follower 42 through groove 58 in a direction parallel to the axis of lancet body 36 is about 0.155". The radius 69 of arc 68 is about 0.064".

Figure 16:
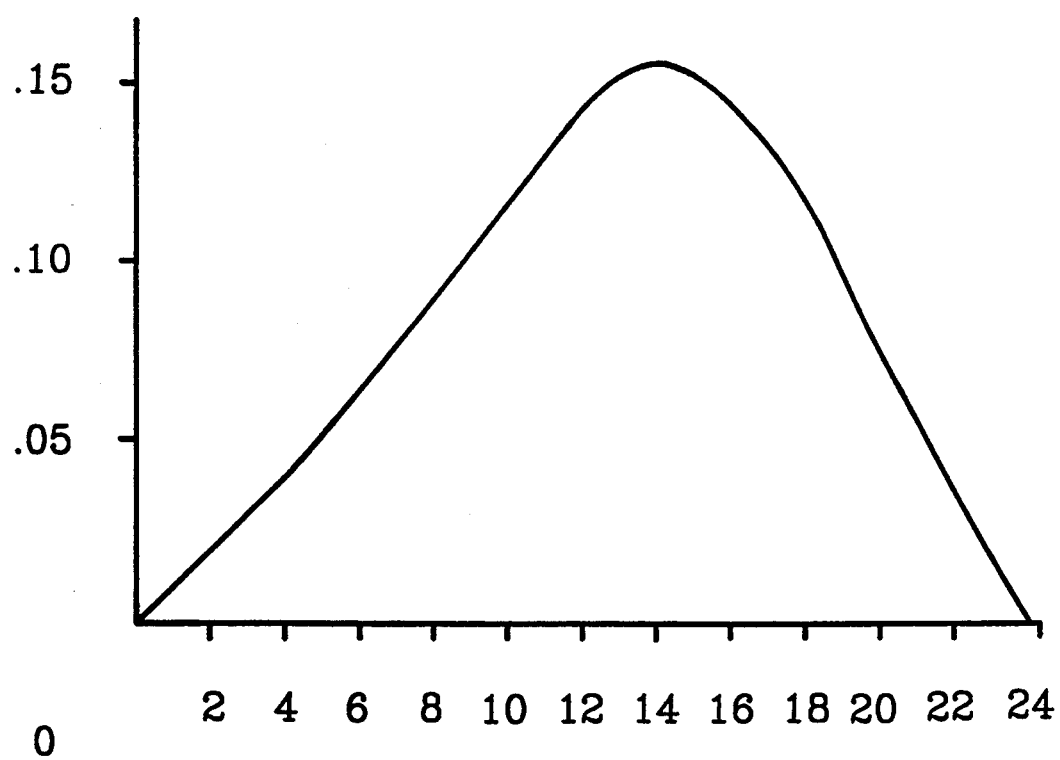
FIG. 16 is a graph of the displacement of the distal tip of the lancet versus the angle of rotation of the arm around the hinge for the embodiment of FIG. 15.

With these parameters, FIG. 16 shows a graph of the displacement of the distal tip 40 of lancet 38 versus the angle of rotation of arm 48 around hinge 50. As can be seen, there is a near linear relationship between the displacement of distal tip 40 and the degree of rotation of arm 48 around hinge 50 from 0° to about 12° and from about 16° to 24° of rotation. However, the near linear relationship between the displacement of distal tip 40 and the degree of rotation of arm 48 around hinge 50 from 0° to about 12° is not the same as the near linear relationship between the displacement of distal tip 40 and the degree of rotation of arm 48 around hinge 50 from about 16° to 24°.

There is less displacement of distal tip 40 per degree of rotation of arm 48 around hinge 50 for the rotation range of 0° to 12°. However, this leads to increased force on the distal tip 40 as it moves along leg 62. The increased force allows the distal tip 40 to more easily penetrate the tissue as the distal tip 40 moves distally.

Correspondingly, there is more displacement of distal tip 40 per degree of rotation of arm 48 around hinge 50 for the rotation range of 16° to 24° than for the rotation range of 0° to 12°. This leads to decreased force on the distal tip 40 as it moves along leg 64. However, less force is needed because the distal tip 40 is moving proximally out the hole in the tissue caused by the distal movement of the distal tip 40. Another consequence of the relatively more displacement of distal tip 40 per degree of rotation of arm 48 around hinge 50 is that distal tip 40 is retracted from the incision in the patient's tissue more quickly than distal tip 40 penetrated the patient's tissue.

As stated, 24° has been found to be the preferred amount of rotation of arm 48 around hinge 50. However, this amount has been determined based, among other things, on the size of the device 2 relative to the user's hand and the relative size of the components of the device 2. It will be clear to those skilled in the art that arm 48 may rotate around hinge 50 by an amount more or less than 24° as the device is made larger or smaller in order to optimize the feel of the device in the user's hand and the amount of travel required to move arm 48 relative to case 8.

Further, although specific lengths, angles and degrees have been given herein, it is to be understood that the specific quantities have been given as the currently understood best mode of implementing the lancet device known to the applicant. As such, the specific quantities are exemplary of those that are preferred to be used. It will be clear to those skilled in the art to vary the specific quantities disclosed as desired to produce devices of varying size and operation.

Figure 18:
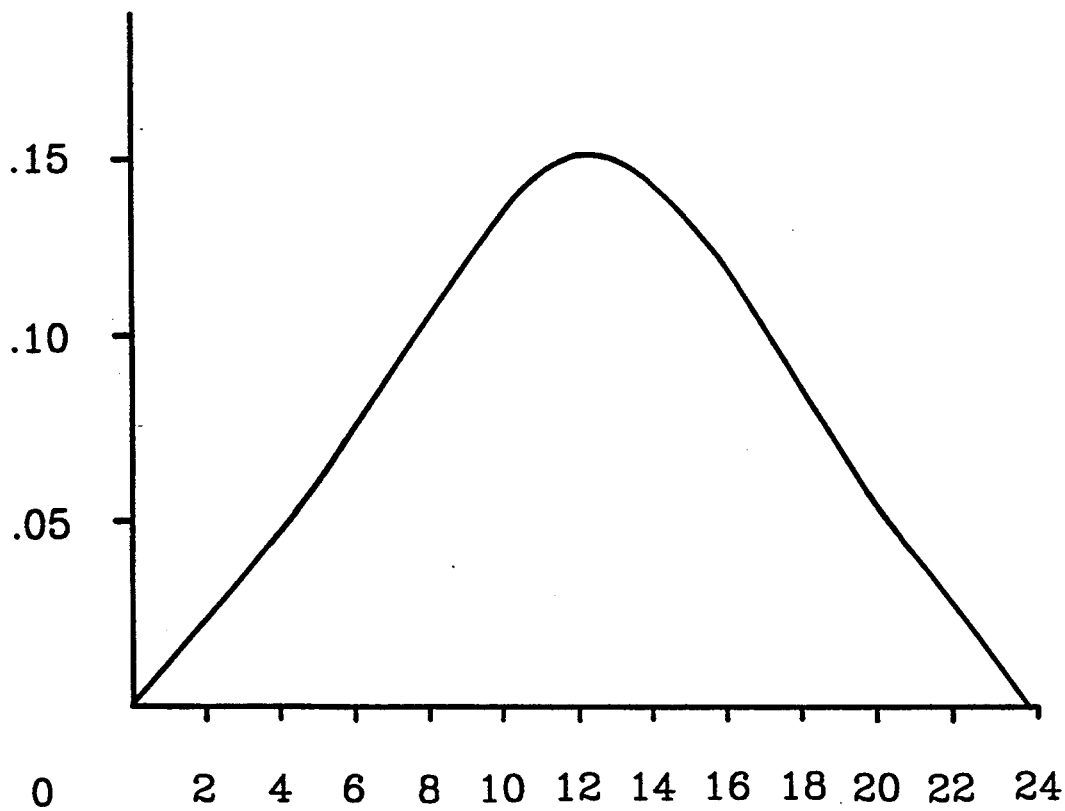
FIG. 18 is a graph of the displacement of the distal tip of the lancet versus the angle of rotation of the arm around the hinge for the embodiment of FIG. 17.
Figure 17:
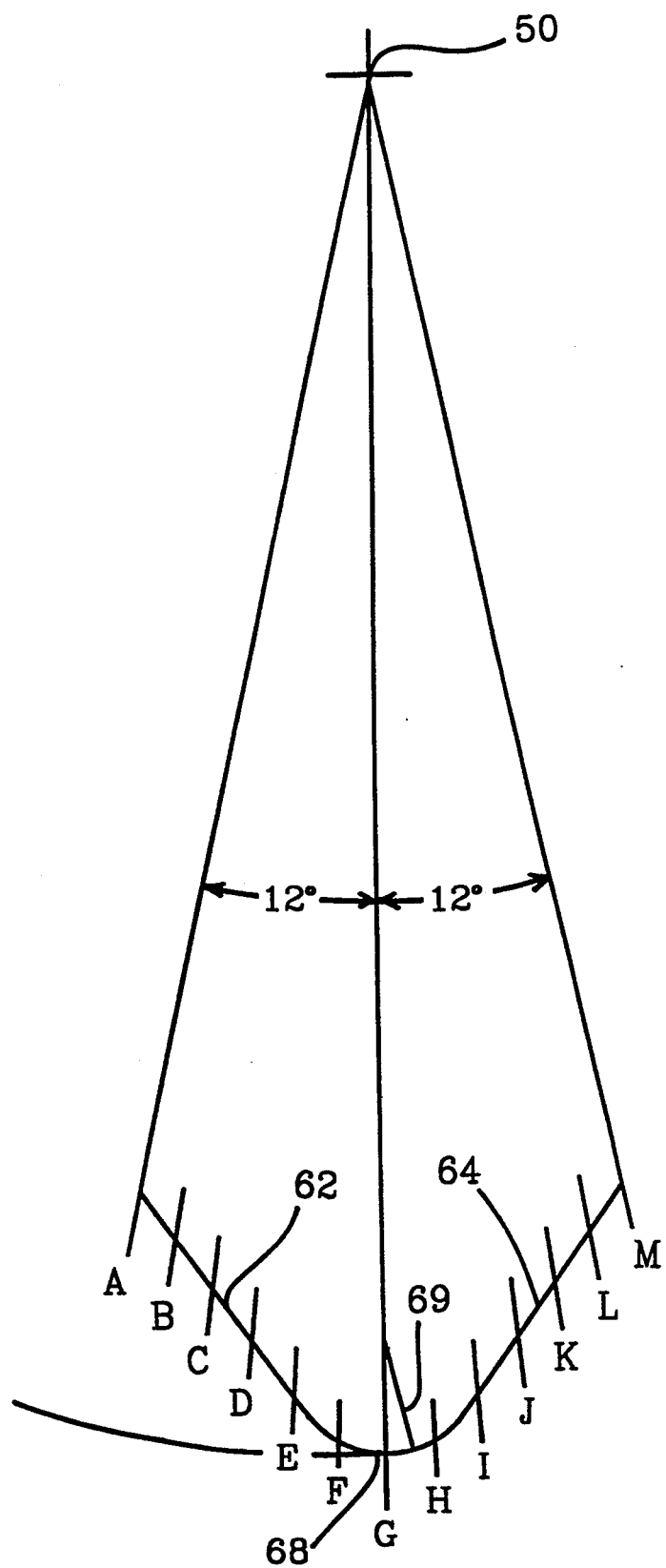
FIG. 17 is a schematic view of the cam follower section and groove of an alternate embodiment of the lancet device.

For example, as shown in FIG. 17, the "lancet most distal" position can correspond to radial G and the angles of legs 62, 64 relative to the axis of motion of lancet body 36 may be equal so that an equal mechanical advantage is obtained as arm 48 moves through its entire range of motion pivoting around hinge 50. FIG. 18 is a graph of the displacement of the distal tip 40 of the lancet 38 versus the angle of rotation of arm 48 around hinge 50 for the embodiment of FIG. 17.

As can be seen, there is also a near linear relationship between the displacement of distal tip 40 and the degree of rotation of arm 48 around hinge 50 from 0° to about 10° and from about 14° to 24° of rotation. However, in this embodiment, the near linear relationship between the displacement of distal tip 40 and the degree of rotation of arm 48 around hinge 50 from 0° to about 10° is the same as the near linear relationship between the displacement of distal tip 40 and the degree of rotation of arm 48 around hinge 50 from about 14° to 24°. Therefore, there is approximately equal displacement of distal tip 40 per degree of rotation of arm 48 around hinge 50 for the rotation range of 0° to 10° and for the rotation range 14° to 24°. This leads to equal force on the distal tip 40 as it moves along leg 62 and along leg 64.

Figure 19:
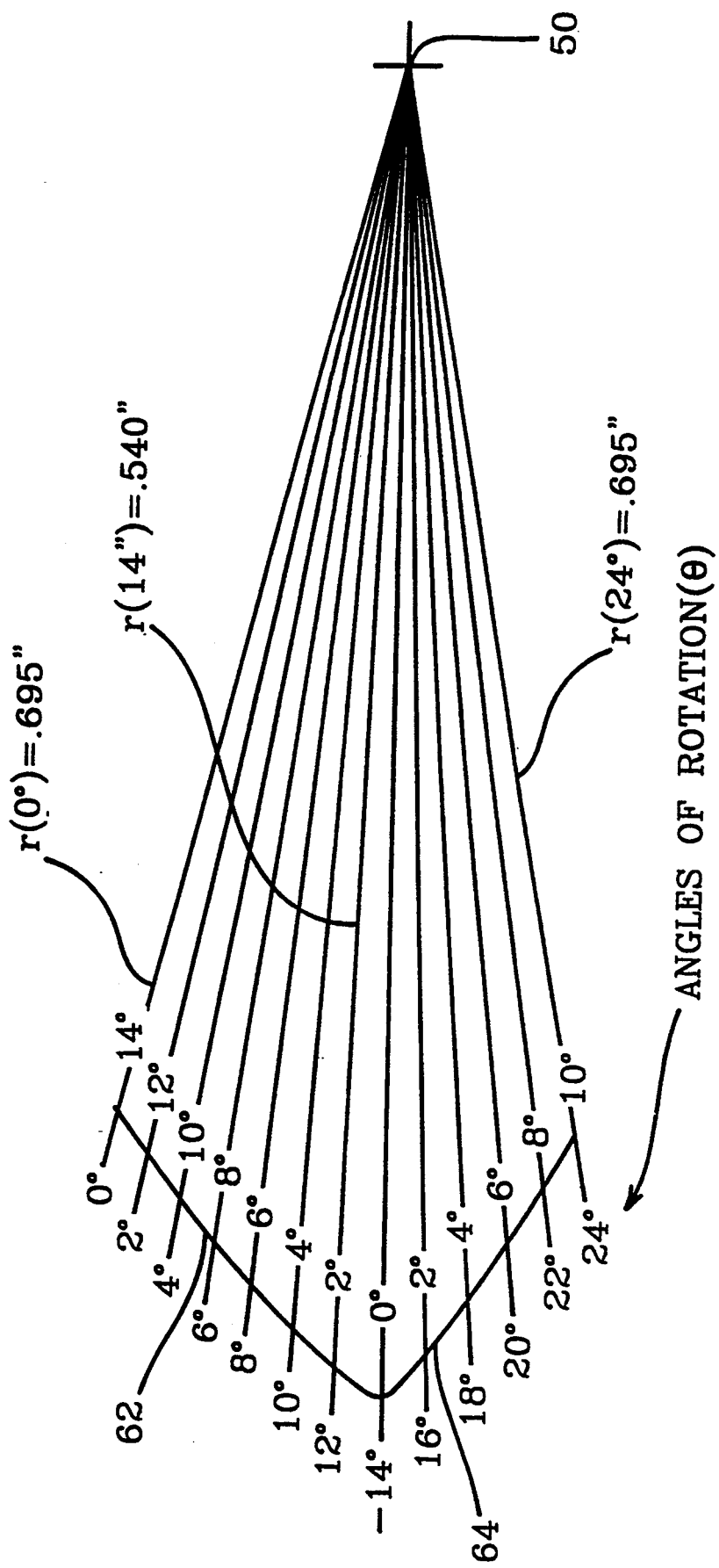
FIG. 19 is a schematic view of the cam follower section and groove of an alternate embodiment of the lancet device.

Other embodiments of the device 2 may have legs 62, 64 being curved or have combinations of curved and straight legs. One example of a legs 62, 64 being curved is shown in FIG. 19. The curves shown in FIG. 19 have been chosen to produce an exactly linear relationship between the displacement of distal tip 40 and the degree of rotation of arm 48 around hinge 50 from 0° to about 14° and from about 14° to 24° of rotation.

In this embodiment, legs 62 and 64 are both curved so that as cam follower 42 is mod along legs 62 and 64, $dr/d\Theta$ =constant, where r is the length of the radial from hinge 50 to the axis of leg 62 or 64 and $\Theta$ is the angle of rotation of arm 48 around hing 50 from the "ready to use" position Solving the equation $dr/d\Theta$ =constant for r and $\Theta$ leads to the solution:

$$r = \text{constant} \times \Theta.$$

In this embodiment, the constant may be different for leg 62 than it is for leg 64. In all other ways, this embodiment operates as described above In particular, the variation in the length r of the radial from hinge 50 to the axis of leg 62 or 64 will produce a corresponding displacement of the distal tip 40 as cam follower 42 moves through legs 62 and 64.

For leg 62 where the angle of rotation of arm 48 around hinge 50 varies from 0° to 14° for the reasons given above, the constant is determined by dividing the maximum change of length of r over the range 0° to 14° by the 14° of movement of arm 48 over the range. Where, as above, the variation of r, and the corresponding displacement of distal tip 40, over the range 0° to 14° is 0.155", the constant is 0.155"/14° or about 0.011"/°. The curve of leg 62 shown in FIG. 19 was determined by plotting the equation $$r(\Theta°) = r(0°) + 0.011''/° \times \Theta$$

over the range $0° \leq \Theta \leq 14°$ where r(0°)=0.695".

For leg 64 where the angle of rotation of arm 48 around hinge 50 varies from about 14° to 24°, also for the reasons given above, the constant is determined by dividing the maximum change of length of r over the range 14° to 24° by the 10° of movement of arm 48 over the range. Where, as above, the variation of r, and the corresponding displacement of distal tip 40, over the range 14° to 24° is 0.155", the constant is 0.155"/10° or about 0.016"/°. The curve of leg 64 shown in FIG. 19 was determined by plotting the equation $$r(\Theta°) = r(14°) - (0.016''/° \times (\Theta° - 14°))$$

over the range $14° \leq \Theta \leq 24°$ where r(24°)=0.695".

In the embodiment of FIG. 19, near the "lancet most distal" position, which corresponds approximately to the H radial, legs 62, 64 would have to be deflected from their respective curved configurations described above to form a transition curve from leg 62 to leg 64.

This transition curve allows cam follower 42 to move in a smooth transition from leg 62 to leg 64. In its simplest form, the transition curve is just a slight gentle rounding of the meeting of legs 62 and 64 at common point 66. The transition curve then intersects the central axes of legs 62, 64.

Figure 20:
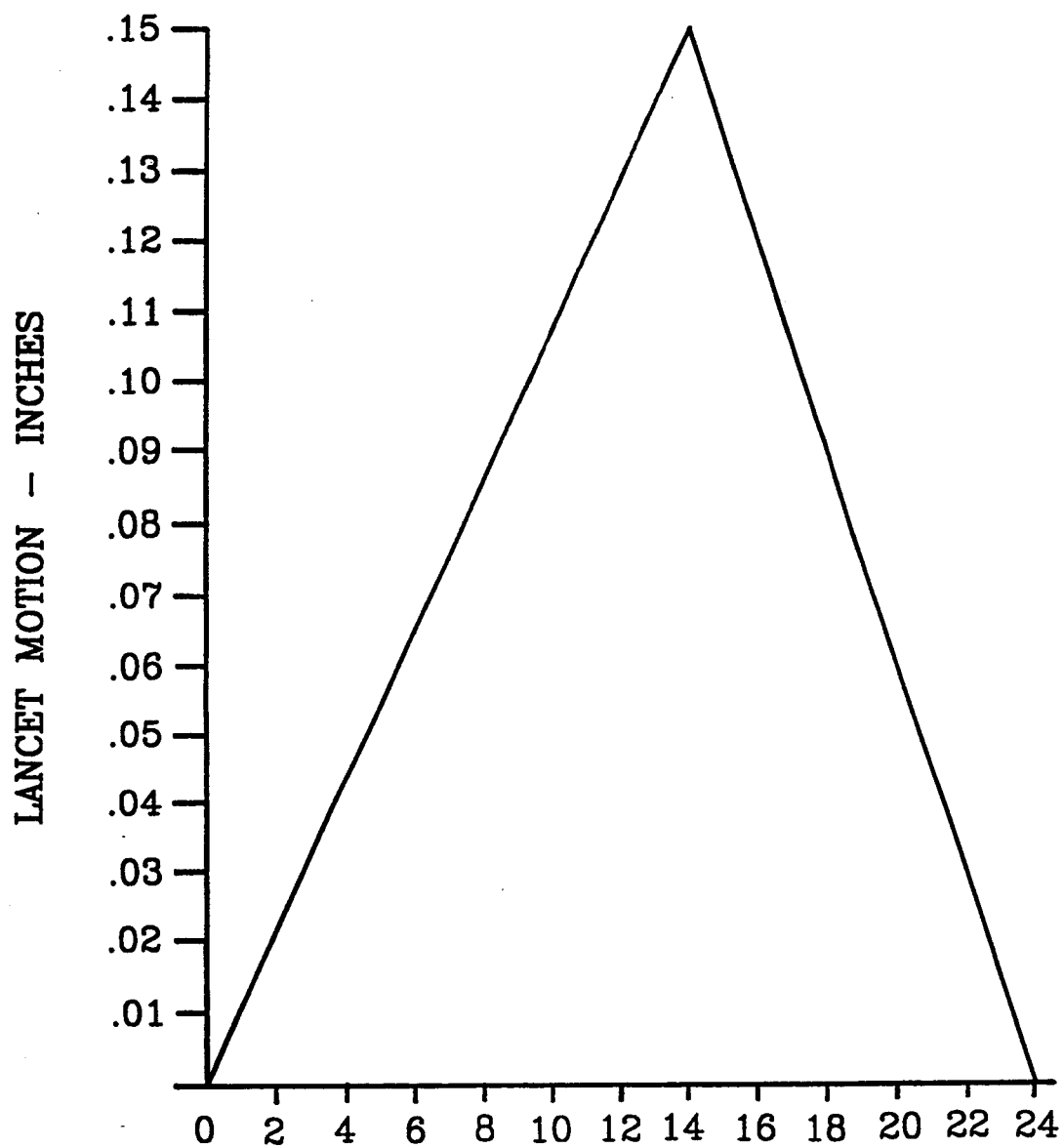
FIG. 20 is a graph of the displacement of the distal tip of the lancet versus the angle of rotation of the arm around the hinge for the embodiment of FIG. 19.

FIG. 20 is a graph of the displacement of the distal tip 40 of the lancet 38 versus the angle of rotation of the arm 48 around the hinge 50 for the embodiment of FIG. 19. As can be seen, the displacement of the distal tip 40 of the lancet 38 versus the angle of rotation of arm 48 around hinge 50 is linear for movement of cam follower 42 in both legs 62 and 64.

In other alternate embodiments of the device 2, legs 62, 64 may have various curvatures or combinations of curves and straight sections. By using desired combinations of straight and curved legs 62, 64, the movement profile of the distal tip 40 of lancet 38 during the movement of arm 48 around hinge 50 may be changed to any desired shape.

In the preferred embodiment of the groove 58, regardless of the shape of legs 62, 64, the ultimate proximal end 70 of leg 62 ends in an enlarged circular opening 72. Opening 72 is offset from the central axis 74 of leg 62 so that the inside surface 76 of leg 62 is straight until the ultimate proximal end 70 of leg 62 is reached. The outside surface 78 of leg 62 has an enlarged radius of curvature at the ultimate proximal end 70 of leg 62. This produces a cradle 80 near the ultimate proximal end 70 of leg 62 to hold cam 42 in the "ready to use" position.

When the device 2 is in the "ready to use" position, cam follower 42 is in contact with cradle 80 so that the axis of linear motion of lancet body 36 intersects cradle 80 at approximately a right angle. When cap 44 is removed, lancet body 36 is pulled distally. This moves cam 42 into contact with cradle 80. This rotation away from case 8 causes cam section 54 to contact the inside surface of outer edge 18 so that arm 48 may not continue to rotate away from case 8.

Because arm 48 may not continue to rotate away from case 8, arm 48 is wedged into a stopped configuration by the contact with the inside surface of outer edge 18. As a result, when lancet body 36 is drawn distally by cap 44 being removed distally, lancet body 36 is prevented from also moving distally by contact with cradle 80.

When the device 2 is to be used, as described hereafter, the device 2 is squeezed so that arm 48 moves toward case 8. As arm 48 moves toward case 8, cam 42 moves out of cradle 80 and into contact with the inside surface 76 of leg 62.

Figure 21:
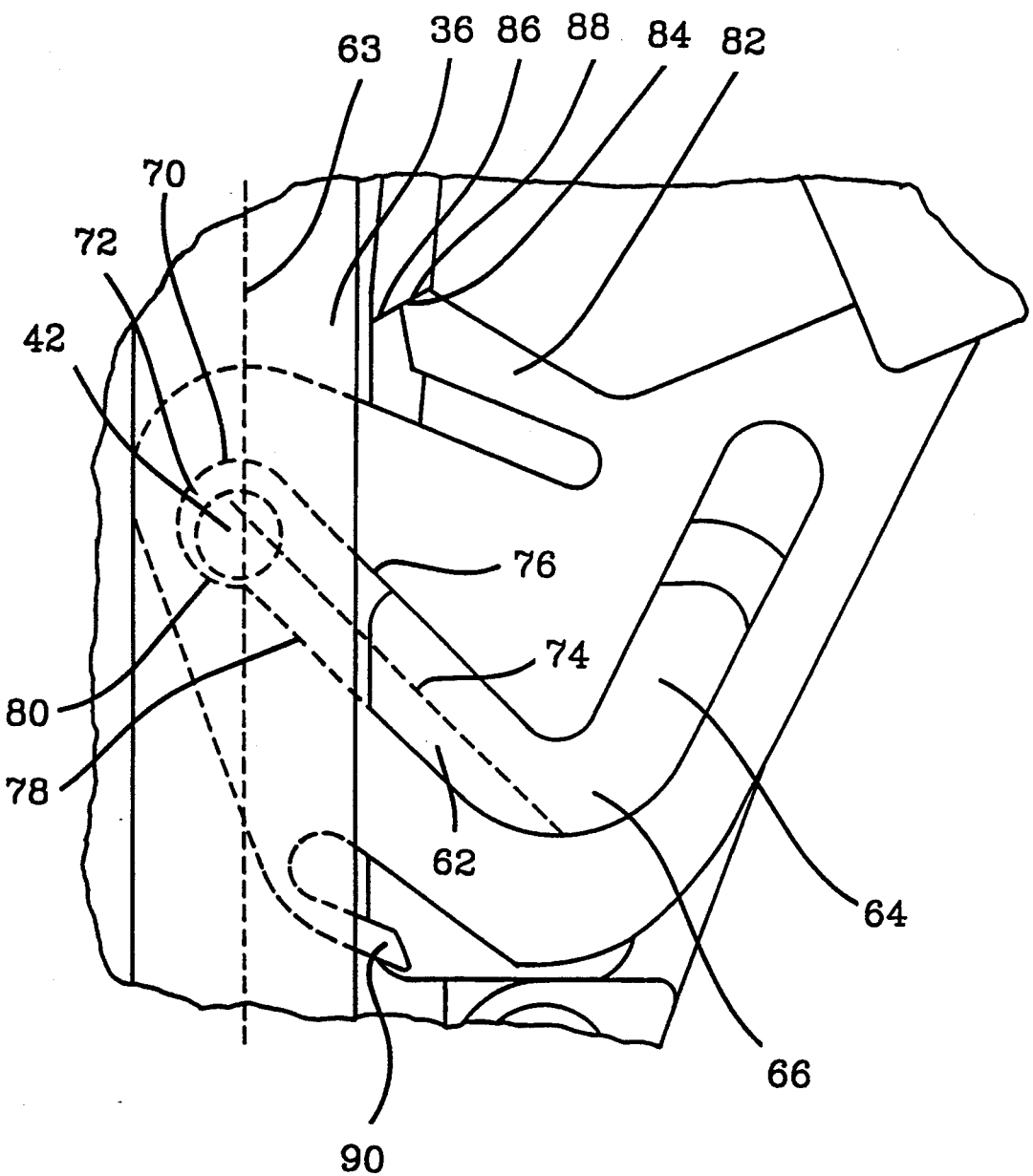
FIG. 21 is a plan view of the assembly that retains the arm in the "ready to use" position.

A start detent arm 82 extends away from the cam section 54 of arm 48 toward case 8 and is shown in more detail in FIG. 21. Start detent arm 82 is made of the same resilient material as the rest of cam section 54. Start detent arm 82 ends at its ultimate end 84 in an oblique angle so that a flat end surface is formed on end 84.

Figure 9:
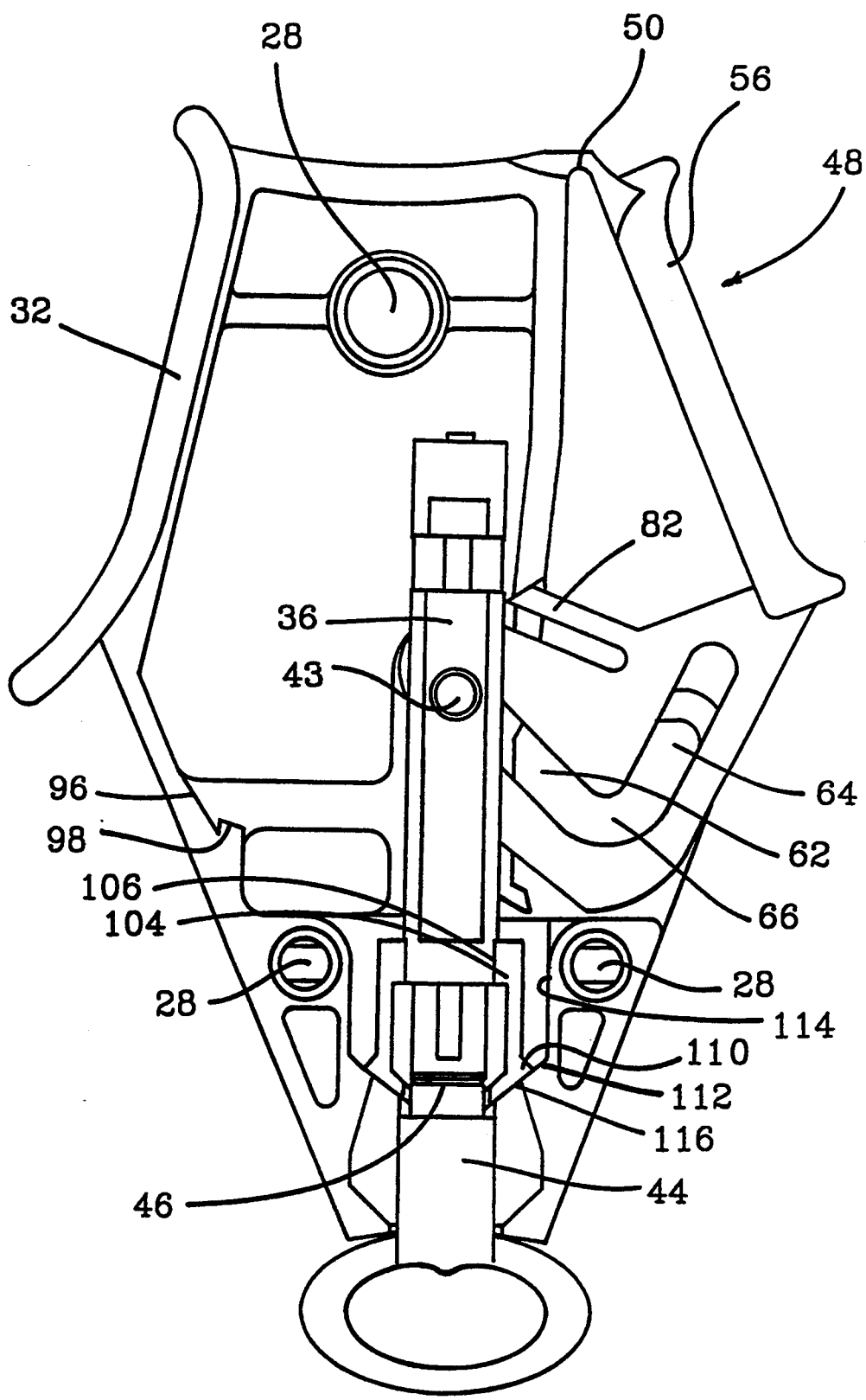
FIG. 9 is a plan view of the lower section with the lancet body in position in the case with the cap covering the lancet tip and the cam follower engaging the groove with the arm in the "ready to use" position.

When arm 48 is in the "ready to use" position shown in FIG. 9, start detent arm 82 contacts a start detent 86 in lower section 10. Start detent 86 is formed in lower section 10 near the outer edge 18-of lower section 10. Start detent 86 has a flat surface 88 that defines the proximal end 4 of slot 60 formed between the outer edges 18, 22 of lower and upper sections 10, 12.

The oblique angle at the ultimate end 84 of start detent arm 82 is such that when arm 48 is in its "ready to use" position, the flat ultimate end 84 of start detent arm 82 is in frictional contact with the flat surface 88 of start detent 86 along the entire surface of ultimate end 84. Frictional contact between start detent arm 82 and start detent 86 inhibits start detent arm 82 from moving across the flat surface 88 of start detent 86 until sufficient force is applied to start detent arm 82 to overcome the frictional force resisting its movement. When sufficient force is applied to start detent arm 82 through force being applied to arm 48, start detent arm 82 will suddenly slide past start detent 86 with a "snap" action. This "snap" action will also allow arm 48 to move with a "snap action" toward case 8.

Figure 22:
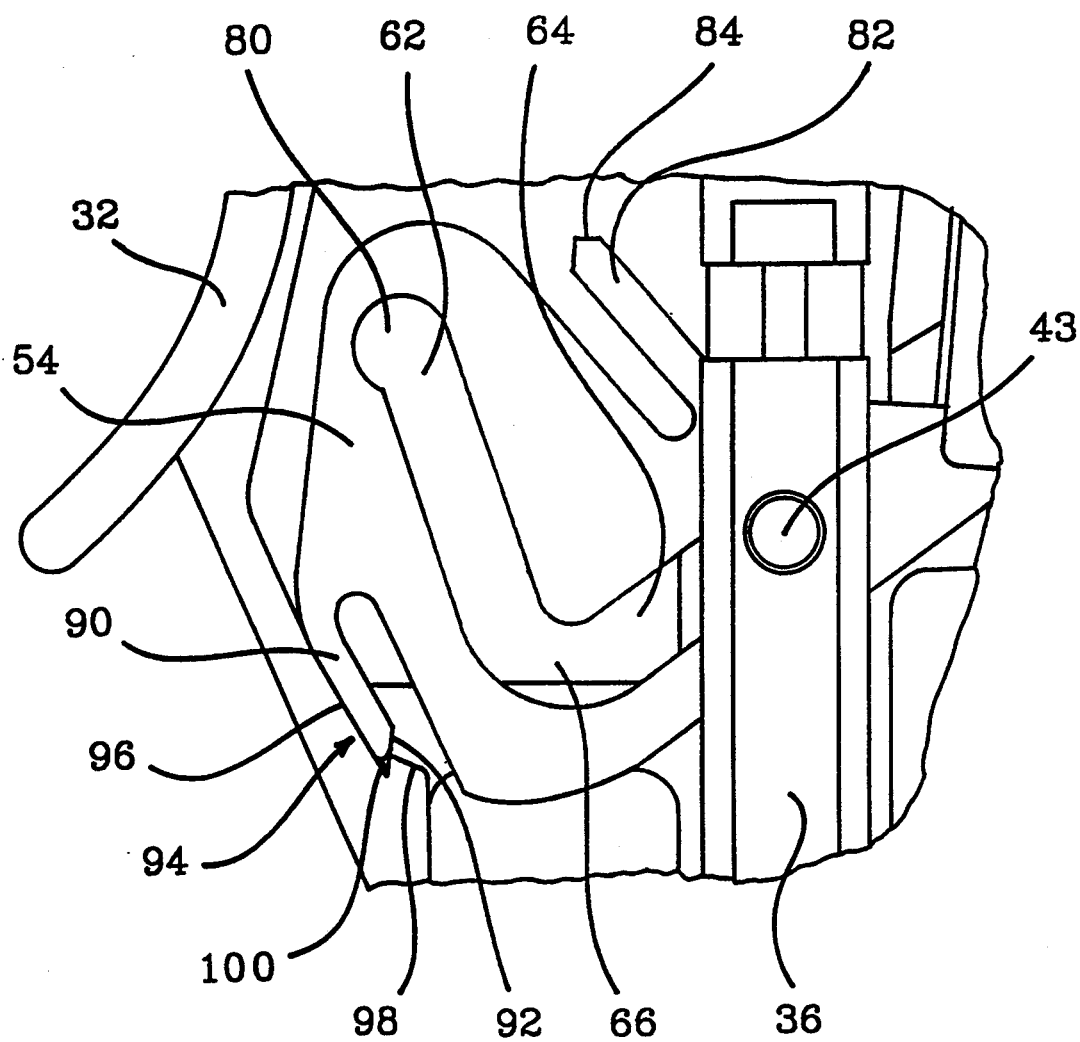
FIG. 22 is a plan view of the assembly that retains the arm in the "already used" position.

As shown in detail in FIG. 22, a locking arm 90 extends away from the distal side of cam section 54 in a distal direction. Locking arm 90 is made of the same resilient material as the rest of cam section 54. Locking arm 90 ends at its ultimate end 92 in an oblique angle so that a flat end surface is formed.

A locking recess 94 is formed along the non-arm side 16 of outer edge 18 of lower section 10. Locking recess 94 has a flat surface 96 extending away from the inner surface of outer edge 18 of lower section 10 toward the interior of lower section 10. Locking recess 94 ends at its most interior end in a lip 98. As arm 48 is moved toward the "used and locked" position from the "lancet most distal" position, locking arm 90 contacts the interior facing surface 100 of lip 98. Continued pressure on cam section 54 causes locking arm 90 to deform and move over lip 98 and into contact with the flat surface 96 of locking recess 94.

The oblique angle of the ultimate end 92 of locking arm 90 is such that when arm 48 is in its "used and locked" position, the ultimate end 92 of locking arm 90 is in contact with the flat surface 96 of locking recess 94 along the majority of the surface of ultimate end 92. Contact between locking arm 90 and lip 98 prevents locking arm 90 from moving back over lip 98. Because locking arm 90 is prevented from moving back over lip 98, arm 48 cannot move away from the "used and locked" position and arm 48 is locked in the "used and locked" position.

Lower section 10 and arm 48 are preferably molded in one piece of a resilient plastic material such as polyethylene or polypropylene. In this way, manufacturing costs are minimized. Although it is preferred to mold these elements of device 2 in one piece, the elements may be formed separately and attached by means well understood by those skilled in the art. Further, upper section 12 and lancet body 36 are also molded of a resilient plastic material such as polyethylene or polypropylene.

Figure 8:
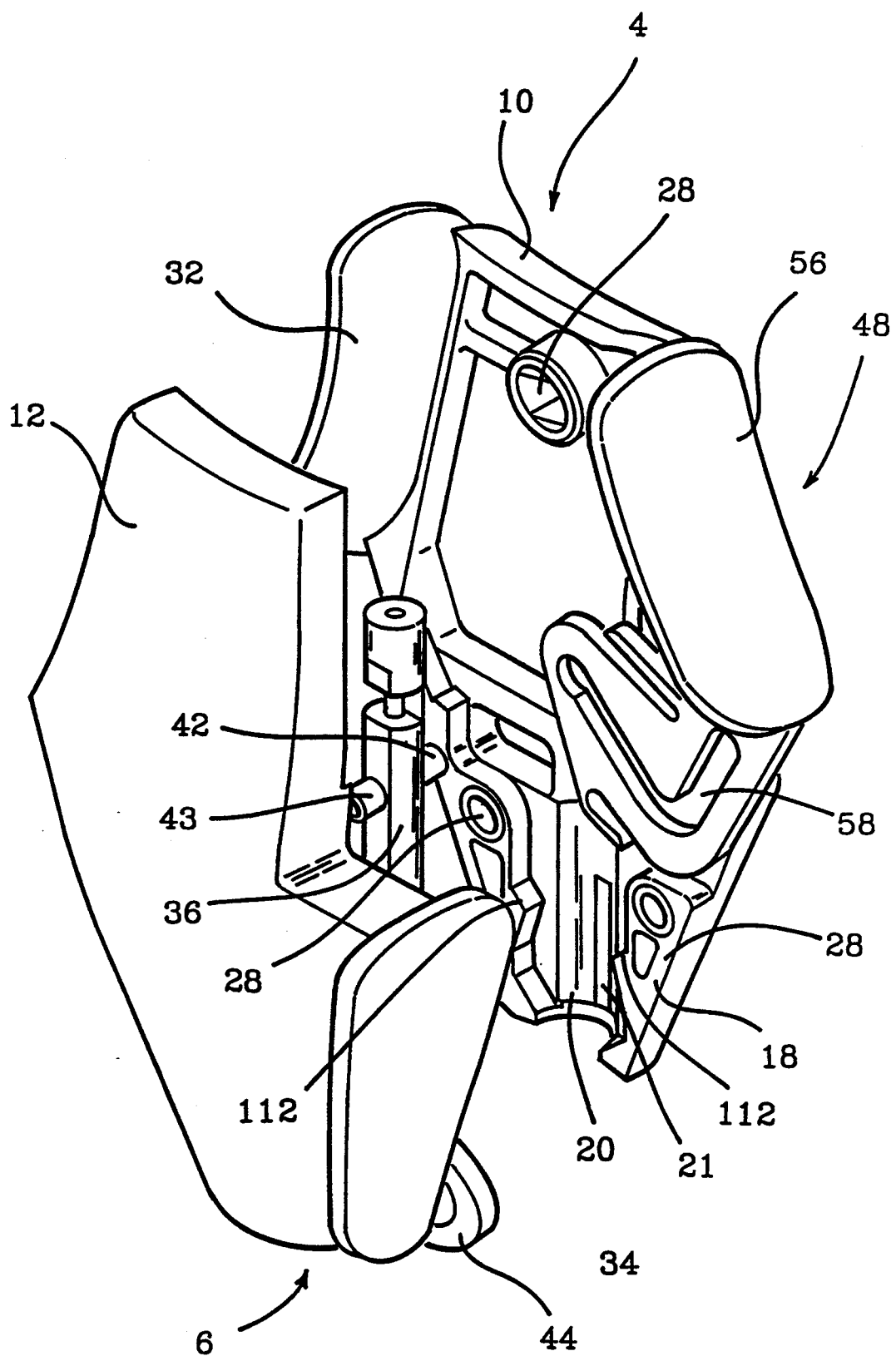
FIG. 8 is an exploded view of the device of FIG. 1.
Figure 23:
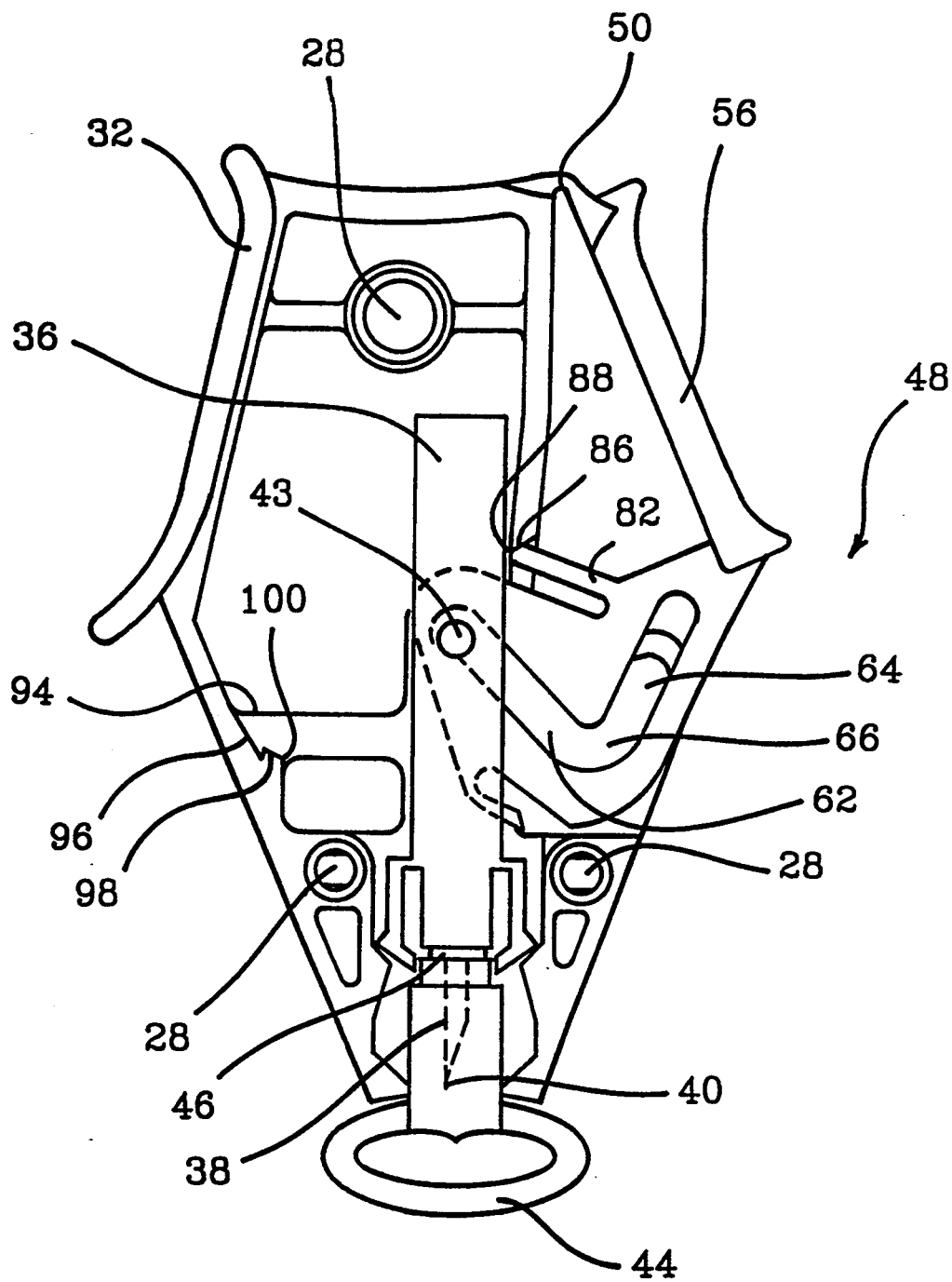
FIG. 23 is a plan view of the invention in use in the preferred embodiment of the lancet device.

FIG. 8 shows the device 2 of FIG. 1 in an exploded configuration. To assemble the device 2, lancet body 36 is placed in lower section recess 20 in lower section 10. Cam follower 42 is placed through groove 58 into contact with positioning slot 27 (FIG. 23). Lancet body 36 and arm 48 will then be in the "ready to use" position shown in FIG. 9. In this position, cam follower 42 is located at the proximal end 70 of leg 62 in contact with cradle 80 and is adjacent the proximal end of positioning slot 27. Also, lancet body 36 is in its most proximal position in lower section recess 20.

As arm 48 is moved to the "ready to use" position, start detent arm 82 moves into frictional contact with start detent 86 as described above. In this position, frictional contact between start detent arm 82 and start detent 86 inhibits arm 48 from moving toward case 8 which in turn prevents lancet body 36 from moving distally. This effectively positions arm 48 in the "ready to use" position until the device 2 is to be used.

To complete the assembly of device 2, upper section 12 is aligned and brought into contact with lower section 10. As upper section 12 is moved into contact with lower section 10, lock tabs 30 contact and mate with lock holes 28 thereby holding lower section 10 in contact with upper section 12 as described above. In this way, lancet body 36 is securely positioned within the chamber 26 formed between lower and upper section recesses 20, 24 so that cam follower 42 is in contact with groove 58 at the proximal end 70 of leg 62.

FIGS. 9-12 show the operation of the device 2. In these Figures, upper section 12 has been removed so that the movement of lancet body 36 relative to lower section 10 may be more clearly seen. However, it is to be understood that in the operating device 2, upper section 12 is in contact with lower section 10 as described above.

FIG. 9 shows the device 2 in its "ready to use" position. In this position, the device 2 may be transported and stored. As can be seen, lancet body 36 is in place in chamber 26 and cam 42 contacts groove 58 at the proximal end 70 of leg 62. Cap 44 encloses the sharp distal tip 40 of lancet 38. Lancet body 36 is in its most proximal position with start detent arm 82 contacting start detent 86 to hold arm 48 in the "ready to use" position which in turn holds lancet body 36 in its most proximal position.

To use the device 2, cap 44 is removed. This is done by grasping cap 44 between the user's finger and thumb and twisting. As explained above, this causes cap 44 to separate from lancet body 36 at break point 46. This causes cap 44 to separate from lancet body 36 at break point 46 leaving the sharp distal tip 40 of lancet 38 exposed beyond the distal end 6 of lancet body 36.

The proximal end of cap 44 is then preferably placed in either hole 23 or hole 23'. There, contact between hole 23 or 23' and the proximal end of cap 44 frictionally retains cap 44 in hole 23. Having both hole 23 and hole 23' extending into the outer surface of the upper and lower sections 12, 10, respectively, allows both right and left handed people to easily remove and store cap 44 in the most convenient hole 23 or 23' while holding device 2 in either the right or left hand. It is particularly important to retain cap 44 with device 2 where the device 2 may be used on or in the vicinity of children so that cap 44 may not be inadvertently swallowed or lodged in the trachea of a child.

Because cap 44 encases the distal tip 40 of lancet 38, cap 44 is in frictional contact between cap 44 and the distal tip 40 of lancet 38. The operation of moving cap 44 distally from contact with the distal end 40 of lancet body 36 causes the distal tip 40 to be drawn distally along with cap 44. However, contact between cam follower 42 and cradle 80, as described above, retains lancet body 36 in its most proximal position.

Figure 10:
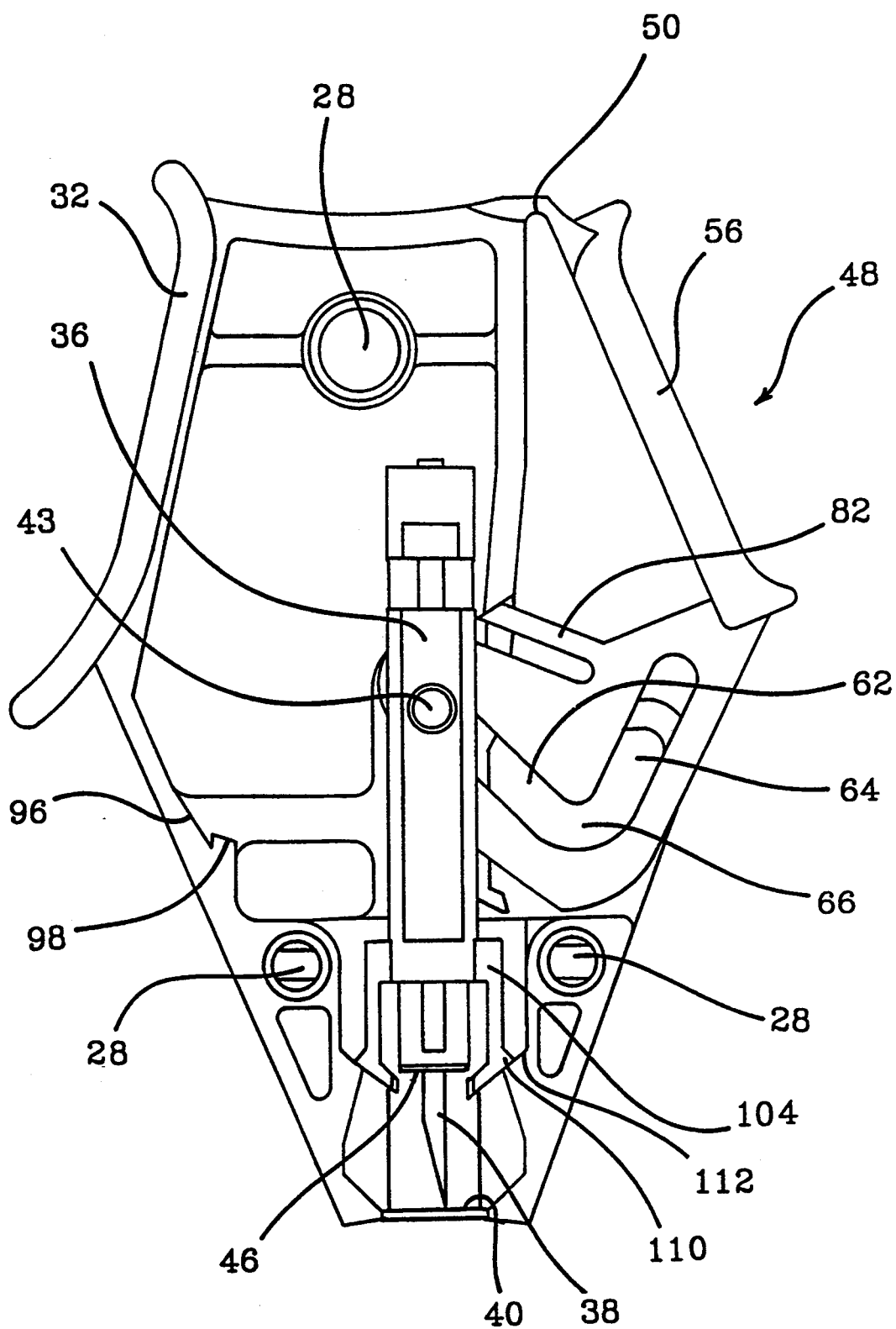
FIG. 10 is a plan view of the device of FIG. 6 with the cap removed from covering the lancet tip.

Because lancet body 36 is in its most proximal position, the ultimate distal tip 40 of lancet 38 does not extend beyond the distal end 6 of lower section 10. In this way, as shown in FIG. 10, the user may not come into contact with the sharp distal tip 40 of lancet 38 even with cap 44 removed.

To use the device 2 to puncture the patient's skin, the user grasps the device 2 between the finger and the thumb placed on finger pads 32, 34 and 56. This forces start detent arm 82 past start detent 86 which allows arm 48 to move toward case 8. This then causes contact between the inside surface 76 of leg 62 and cam follower 42 which forces cam follower 42, and consequently lancet body 36, distally.

Further movement of finger pad 56 causes arm 48 to move toward case 8 until arm 48 reaches the "lancet most distal" position. In this position, cam follower 42 is located at the common point 66 where legs 62, 64 meet. This position is the most distal position of cam follower 42 as it moves along groove 58. Because cam follower 42 is in its most distal position, lancet body 36 is also in its most distal position. This causes the distal tip 40 to be moved to its most distal position. In this position, the geometry of device 2 is such that the distal tip 40 extends beyond the distal end 6 of case 8. In this position, the geometry of device 2 is such that the distal tip 40 extends beyond the distal end 6 of case 8.

Further squeezing of finger pad 32 towards finger pads 34, 56 causes arm 48 to continue to move toward case 8 until the "already used" configuration shown in FIG. 12 is reached.

Further squeezing of finger pad 56 causes arm 48 to continue to move toward case 8 until the "used and locked" configuration shown in FIG. 12 is reached. During this operation, cam follower 42 moves into leg 64 where contact between cam follower 42 and the outside surface 102 of leg 64 causes cam follower 42 to move proximally along leg 64. This proximal movement of cam follower 42 causes lancet body 36 to move proximally so that the distal tip 40 of lancet 38 is moved entirely back within chamber 26. In the "already used" position, contact between locking arm 90 and locking detent 94, as described above, locks the device 2 with the lancet body 36 in its most proximal position within chamber 26 and arm 48 moved closest to case 8.

In the "used and locked" position, contact between locking arm 90 and locking recess 94, as described above, locks the device 2 with the lancet body 36 in its most proximal position within chamber 26 and arm 48 moved closest to case 8.

The act of squeezing finger pad 56 from the "ready to use" position shown in FIG. 10 to the "used and locked" position shown in FIG. 12 takes place in a rapid continuous motion. In an alternate embodiment of the lancet device, lower section recess 20 tapers slightly at its distal end to provide an opening that is slightly narrower than the diameter of the rest of lower section recess 20.

In an alternate embodiment of the lancet device, lower and upper section recesses 20, 24 have an inwardly directed abutment at their distal ends to provide an opening to the distal end of chamber 26 that is slightly narrower than the diameter of the rest of chamber 26.

The distal end of lancet body 36 is also tapered. In this embodiment, the device 2 causes the tapered distal end of the lancet body 36 to firmly contact the tapered distal end of chamber 26 slightly before cam 42 reaches the common point 66 between legs 62, 64 of groove 58.

In this embodiment, the device 2 causes the tapered distal end of the lancet body 36 to firmly contact the abutment at the distal end of chamber 26 slightly before cam follower 42 reaches the common point 66 between legs 62, 64 of groove 58. This contact controls the extent that the distal tip 40 of lancet 38 extends from the distal end of case 8, and enhances the "snap" feeling while "squeezing" finger pads 32, 34 and 56 together. Because the tapered distal end of lancet body 36 contacts the tapered distal end of chamber 26 before cam follower 42 reaches the common point 66 between legs 62, 64 of groove 58, as cam follower 42 moves past through the common point 66 and passes its most distal position, the geometry of the device 2 causes arm 48 to flex slightly and then relax as cam follower 42 moves from leg 62 to leg 64.

Further movement of finger pads 32 towards finger pads 34, 56 causes arm 48 to move toward case 8 until arm 48 reaches the "lancet most distal" position. As a result, the elements described above are identical in form and function in this embodiment unless stated otherwise hereafter.

In this embodiment, the arm 48 pivoting around hinge 50 is replaced with an arm 120 that slides transverse to the axis of lancet body 36. Arm 120 has a proximal side 122 and a parallel distal side 124 separated by a distance M.

A proximal channel guide 128 and a parallel distal channel guide 130 are formed in lower section 10. Guides 128 and 130 protrude within lower section 10 and form a channel 132 between guides 128 and 130. Channel 132 receives arm 120 between proximal channel guide 128 and distal channel guide 130. Contact between proximal channel guide 128 and proximal side 122 and distal channel guide 130 and distal side 124, respectively, constrains arm 120 to movement transverse to the axis of lancet body 36.

A finger pad 126 is attached to the arm side 14 of arm 120. Finger pad 126 extends across the entire arm side 14 of arm 120. Finger pad 126 is preferably substantially planar with curved ends. However, finger pad 126 may also be slightly curved along its entire length to allow the user's thumb to be more easily retained thereon. Finger pad 126 may also have means, such as a rough surface to produce a high friction outer surface, to prevent the user's thumb from sliding along finger pad 126.

Arm 120 also has a groove 58 located therein that contacts cam follower 42 exactly as described above. Groove 58 may have any of the shapes described above and shown in the Figures in connection with other embodiments of the lancet device.

However, in this embodiment, the embodiments of groove 58 having straight legs 62, 64 will produce a linear relationship between the motion of the distal tip 40 versus the transverse movement of arm 120 as cam follower 42 moves through the straight parts of legs 62, 64. This is because arm 120 is moving in a transverse direction relative to cam follower 42 instead of in an arc so that a constant angle of contact is formed between cam follower 42 and the inside and outside surfaces 76, 102, respectively, of legs 62, 64.

Although the embodiment of groove 58 shown in FIG. 19 and described above may be used in this embodiment, its use here will not produce a linear displacement of distal tip 40 per amount of transverse movement of arm 120. Instead, its use will produce a nonlinear relationship between the displacement of distal tip 40 and the movement of arm 120 transverse to the lancet body 36. This is because arm 120 is moving in a transverse direction relative to cam follower 42 instead of in an arc. Therefore, a varying angle of contact is formed between cam follower 42 and the inside and outside surfaces 76, 102, respectively, of legs 62, 64.

A start detent arm 82 extends away from proximal side 122 of arm 120 toward case 8 at an angle to proximal side 122. Start detent arm 82 is made of the same resilient material as the rest of arm 120. Start detent arm 82 ends at its ultimate end 84 in an oblique angle so that a flat end surface is formed on end 84.

Figure 24:
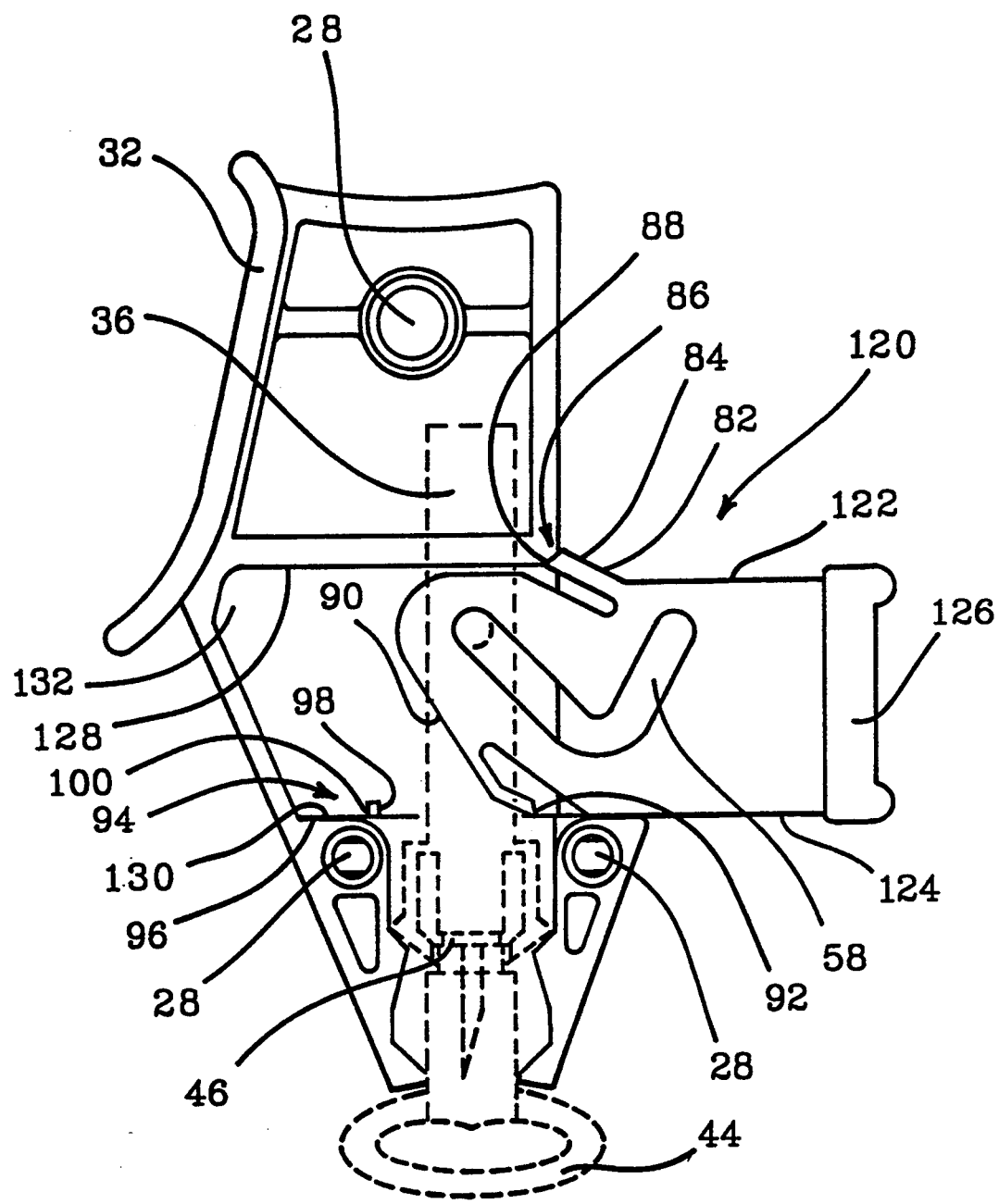
FIG. 24 is a plan view of the lower section and arm of an alternate embodiment of the lancet device in the "ready to use" position with the lancet body in place.

When arm 120 is in the "ready to use" position shown in FIG. 24, start detent arm 82 contacts a start detent 86 in lower section 10. Start detent 86 is formed in lower section 10 near the outer edge 18 of lower section 10. Start detent 86 has a flat surface 88 at the edge of proximal channel guide 128 and the outer edge 18 of lower section 10 proximal to channel 132.

The oblique angle at the ultimate end 84 of start detent arm 82 is such that when arm 120 is in its "ready to use" position, the flat ultimate end 84 of start detent arm 82 is in frictional contact with the flat surface 88 of start detent 86 along the entire surface of ultimate end 84. Frictional contact between start detent arm 82 and start detent 86 inhibits start detent arm 82 from moving across the flat surface 88 of start detent 86 until sufficient force is applied to start detent arm 82 to overcome the frictional force resisting its movement.

When sufficient force is applied to start detent arm 82 through force being applied to arm 120, start detent arm 82 will suddenly slide past start detent 86 with a "snap" action. This "snap" action will also allow arm 120 to move with a "snap action" toward case 8.

A locking arm 90 extends distally away from the non-arm side 16 of arm 120. Locking arm 90 is made of the same resilient material as the rest of arm 120. Locking arm 90 ends at its ultimate end 92 in an oblique angle so that a flat end surface is formed.

A locating recess 134 is formed at the intersection of the non-arm side 16 of the lower section recess 20 and distal channel guide 130. Locating recess 134 has a distal flat surface 136 that is open to lower section recess 20 on the non-arm side 16 of locating recess 134. Flat surface 136 is essentially parallel to distal channel guide 130.

A lip 138 defines the arm side 14 of flat surface 136 and extends perpendicular to both the flat surface 136 and distal channel guide 130. When arm 120 is in the "ready to use" position, the ultimate end 92 of locking arm 90 contacts lip 138. This contact between end 92 and lip 138 prevents arm 120 from moving out of channel 132 and consequently retains arm 120 within channel 132.

A locking recess 94 is formed at the non-arm side 16 of distal channel guide 130. Locking recess 94 has a flat surface 96 collinear with distal channel guide 130. Locking recess 94 ends at its most interior end in a lip 98. As arm 120 is moved toward the "used and locked" position from the "lancet most distal" position, locking arm 90 contacts the interior facing surface 100 of lip 98. Continued pressure on arm 120 causes locking arm 90 to deform and move over lip 98 and into contact with the flat surface 96 of locking recess 94.

The oblique angle of the ultimate end 92 of locking arm 90 is such that when arm 120 is in its "used and locked" position, the ultimate end 92 of locking arm 90 is in contact with the flat surface 96 of locking recess 94 along the majority of the surface of ultimate end 92. Contact between locking arm 90 and lip 98 prevents locking arm 90 from moving back over lip 98. Because locking arm 90 is prevented from moving back over lip 98, arm 120 cannot move away from the "used and locked" position and arm 120 is locked in the "used and locked" position.

The invention has been described in connection with particular embodiments of the lancet device. It however is clear that changes and modifications may be made to the description made herein and still be within the scope of the claims. Further, obvious changes and modifications will occur to those skilled in the art.

I claim:

1. A safety device for selectively preventing movement of a sharp lancet tip out of a lancet device of the type having a linearly movable and retractable lancet tip, the lancet tip substantially enclosed in a lancet body having a proximal and a distal end and a central axis, the sharp lancet tip extending distally from the lancet body, the lancet body also having a removable cap surrounding the lancet tip, the cap having an outer surface, the lancet device having a case having a patient contacting distal end and an opposed proximal end, the case having a chamber at its distal end, the chamber open to the distal end of the case, the chamber containing the lancet, the lancet device having an assembly for linearly and consecutively moving the sharp tip out of the distal end of the case and then back into the distal end of the case along the central axis of the lancet, the safety device comprising:

the distal end of the lancet body having a pair of retainer arms that extend away from the lancet body on opposite sides of the lancet body parallel to the central axis of the lancet body, the distal end of the retainer arms extending slightly beyond the distal end of the lancet body and directed toward the central axis of the lancet body, each retainer arm having a stop located near the distal end of the retainer arms that extends from each of the retainer arms away from the central axis of the lancet body, the retainer arms contacting the outer surface of the cap;

the chamber having a pair of retainer arm supports located along the inner surfaces of the chamber on opposite sides of the chamber, the retainer arm supports jutting away from the inner surfaces at an obtuse angle as viewed by moving distally along the inner surfaces of the chamber, the stops abutting the corresponding retainer arm supports along the distal surface of the stops when the lancet body is in its most proximal position within the chamber;

whereby, with the cap in place around the distal tip of the lancet, any force applied to the lancet body by the lancet device to move the lancet body distally causes the stops to contact the retainer arm supports, where, because the retainer arm supports are angled, as the stops are pressured to move distally, contact between the stops and the retainer arm supports deflects the stops toward the axis of the lancet body where the distal ends of the retainer arms contact the outer surface of the cap so that the stops cannot move clear of contact with the retainer arm supports thereby preventing the retainer arms, and consequently the lancet body, from moving distally; and, whereby, after the cap is removed so that the lancet device may be used to produce a drop of blood from a patient and the lancet device puts pressure on the lancet body to move the lancet body distally, distal pressure on the lancet body is transferred to the retainer arms and to the stops so that as the stops are pressured to move distally, contact between the retainer arm supports and the stops again causes the stops to deflect toward the axis of the lancet body, but because the distal ends of the retainer arms do not contact the outer surface of the cap, the retainer arms may move toward the axis of the lancet body to a position clear of the retainer arm supports thereby allowing the retainer arms, and consequently the lancet body, to move distally so that the distal tip of the lancet may move beyond the distal end of the device.

2. A safety device for selectively preventing movement of a sharp lancet tip out of a lancet device of the type having a linearly movable and retractable lancet tip, the lancet tip substantially enclosed in a lancet body having a proximal and a distal end and a central axis, the sharp lancet tip extending distally from the lancet body, the lancet body also having a cap surrounding the lancet tip, the cap having an outer surface, the lancet device having a case having a patient contacting distal end and an opposed proximal end, the case having a chamber at its distal end, the chamber open to the distal end of the case, the chamber containing the lancet, the lancet device having an assembly for linearly and consecutively moving the sharp tip out of the distal end of the case and then back into the distal end of the case along the central axis of the lancet, the safety device comprising:

a lancet body having a proximal and a distal end and a central axis, the lancet body having a sharp lancet tip extending distally from the lancet body, the lancet body, the distal end of the lancet body having a pair of retainer arms that extend away from the lancet body on opposite sides of the lancet body parallel to the central axis of the lancet body, the distal end of the retainer arms extending slightly beyond the distal end of the lancet body and directed toward the central axis of the lancet body, each retainer arm having a stop located near the distal end of the retainer arms that extends from each of the retainer arms away from the central axis of the lancet body;

a removable cap surrounding the lancet tip, the cap having an outer surface wherein the retainer arms contact the outer surface of the cap when the cap surrounds the lancet tip;

a case having a patient contacting distal end and an opposed proximal end, the case having a chamber at its distal end, the chamber open to the distal end of the case, the chamber containing the lancet body, the chamber having a pair of retainer arm supports located along the inner surfaces of the chamber on opposite sides of the chamber, the retainer arm supports jutting away from the inner surfaces at an obtuse angle as viewed by moving distally along the inner surfaces of the chamber, the stops abutting the corresponding retainer arm supports along the distal surface of the stops when the lancet body is in its most proximal position within the chamber;

means for linearly and consecutively moving the sharp lancet tip out of the distal end of the case and then back into the distal end of the case along the central axis of the lancet body;

whereby, with the cap in place around the distal tip of the lancet, any force applied to the lancet body by the lancet device to move the lancet body distally causes the stops to contact the retainer arm supports, where, because the retainer arm supports are angled, as the stops are pressured to move distally, contact between the stops and the retainer arm supports deflects the stops toward the axis of the lancet body where the distal ends of the retainer arms contact the outer surface of the cap so that the stops cannot move clear of contact with the retainer arm supports thereby preventing the retainer arms, and consequently the lancet body, from moving distally; and, whereby, after the cap is removed so that the lancet device may be used to produce a drop of blood from a patient and the lancet device puts pressure on the lancet body to move the lancet body distally, distal pressure on the lancet body is transferred to the retainer arms and to the stops so that as the stops are pressured to move distally, contact between the retainer arm supports and the stops again causes the stops to deflect toward the axis of the lancet body, but because the distal ends of the retainer arms do not contact the outer surface of the cap, the retainer arms may move toward the axis of the lancet body to a position clear of the retainer arm supports thereby allowing the retainer arms, and consequently the lancet body, to move distally so that the distal tip of the lancet may move beyond the distal end of the device.

3. The device of claim 2 wherein the case includes a lower section and an opposed congruent upper section.

4. The device of claim 3 wherein the lower section is locked into contact with the upper section thereby forming the case and the chamber.

5. The device of claim 4 wherein the lower section in locked into contact with the upper section by mating of lock holes in the lower section and corresponding lock tabs that extend away from the upper section, or vice versa.

6. The device of claim 3 wherein the lower section and upper section are each substantially concave shaped; and, wherein the lower section and the upper section are joined together to form a substantially hollow case.

7. The device of claim 3 wherein the lower section and the upper section each have a generally planar outer edge that extends around the outer periphery of the lower section and upper section, respectively.

8. The device of claim 3 wherein the lower section includes a lower section recess formed in the interior of the lower section that extends from the distal end of the lower section proximally, the lower section recess having a distal end, and wherein the upper section includes an upper section recess formed in the interior of the upper section that extends from the distal end of the upper section proximally, the upper section recess having a distal end;

whereby lower section recess and the upper section recess form the chamber when the lower section and the upper section are joined together.

9. The device of claim 8 wherein the lower section recess and the upper section recess are both half cylindrical and open at their respective distal ends and wherein the lower section recess and the upper section recess are aligned to form a cylindrical chamber that is open at the distal end of the device.

10. The device of claim 8 wherein the central axis of the lower section recess is aligned with the planar outer edge of the lower section, and wherein the central axis of the upper section recess is aligned with the planar outer edge of the upper section.

11. The device of claim 8 wherein the lower and upper section recesses also each have an elongated recess slot that extends into the lower and upper section, respectively, from the outer edges of the lower and upper section recesses, respectively, and wherein the axes of the recess slots are aligned with the axes of the lower and upper section recesses, respectively.

12. The device of claim 8 wherein the lower and upper sections also each have an elongated positioning slot located proximal to the lower and upper section recesses, respectively, an]wherein the axis of the positioning slots are aligned with of lower and upper section recesses, respectively.

* * * * *